United States Patent
Raptis et al.

(10) Patent No.: US 12,251,401 B2
(45) Date of Patent: *Mar. 18, 2025

(54) SYNTHESIS AND ANTIMICROBIAL USES OF DINUCLEAR SILVER(I) PYRAZOLATES

(71) Applicants: Raphael G. Raptis, Miami, FL (US); Indranil Chakraborty, Miami, FL (US); Shambhu Kandel, Miami, FL (US)

(72) Inventors: Raphael G. Raptis, Miami, FL (US); Indranil Chakraborty, Miami, FL (US); Shambhu Kandel, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/378,009

(22) Filed: Oct. 9, 2023

(65) Prior Publication Data

US 2024/0050469 A1 Feb. 15, 2024

Related U.S. Application Data

(60) Division of application No. 17/513,990, filed on Oct. 29, 2021, now Pat. No. 11,779,598, which is a
(Continued)

(51) Int. Cl.
*A61K 33/38* (2006.01)
*A61P 31/04* (2006.01)
(Continued)

(52) U.S. Cl.
CPC .............. *A61K 33/38* (2013.01); *A61P 31/04* (2018.01); *C07F 1/005* (2013.01); *C07F 9/65848* (2013.01)

(58) Field of Classification Search
CPC ......... A61K 33/38; A61P 31/04; C07F 1/005; C07F 9/65848
See application file for complete search history.

(56) References Cited

U.S. PATENT DOCUMENTS 5,928,174 A 7/1999 Gibbins
6,355,858 B1 3/2002 Gibbins
(Continued)

FOREIGN PATENT DOCUMENTS

FR 2881743 A1 8/2006

OTHER PUBLICATIONS

Guo et al., "An Acetylacetone or a Pyrazole? Both! 3-(3,5-Dimethyl-pyrazol-4-yl)pentane-2,4-dione as a Ditopic Ligand", Crystal Growth & Design, 2016,16, 5127-5135. (Year: 2016).*
(Continued)

*Primary Examiner* — Jianfeng Song
(74) *Attorney, Agent, or Firm* — SALIWANCHIK, LLOYD & EISENSCHENK

(57) ABSTRACT

Novel dinuclear silver(I) pyrazolido complexes and methods of synthesizing them are provided. Advantageously, the novel silver(I) pyrazolido complexes have excellent antimicrobial activity and methods of using said complexes to treat bacterial, fungal, and viral infections are also provided.

6 Claims, 31 Drawing Sheets

Related U.S. Application Data continuation of application No. 16/932,075, filed on Jul. 17, 2020, now Pat. No. 11,160,829, which is a continuation of application No. 16/456,834, filed on Jun. 28, 2019, now Pat. No. 10,828,327.

(60) Provisional application No. 62/722,664, filed on Aug. 24, 2018.

(51) Int. Cl.
*C07F 1/00* (2006.01)
*C07F 9/6584* (2006.01)

(56) References Cited

U.S. PATENT DOCUMENTS

| | | |
|---|---|---|
| 6,605,751 B1 | 8/2003 | Gibbins et al. |
| 6,897,349 B2 | 5/2005 | Gibbins et al. |
| 7,576,255 B2 | 8/2009 | Gibbins et al. |
| 9,980,497 B2 | 5/2018 | Gawande et al. |
| 10,357,470 B2 | 7/2019 | Gawande et al. |
| 2016/0015047 A1 | 1/2016 | Gawande et al. |

OTHER PUBLICATIONS

Ardizzoia, G.A., et al., "Silver(I) Pyrazolate. Synthesis and X-Ray and 31P-NMR Characterization of Triphenylphosphine Complexes and Their Reactivity toward Heterocumulenes", Inorganic Chemistry, 1997, 36: 2321-2328.

Atrián-Blasco, E., et al., "Copper(I) targeting in the Alzheimer's disease context: a first example using the biocompatible PTA ligand." Metallomics, 2015, 7: 1229-1232.

Jaros, S.W., et al., "Silver(I) 1,3,5-Triaza-7-phosphaadamantane Coordination Polymers Driven by Substituted Glutarate and Malonate Building Blocks: Self-Assembly Synthesis, Structural Features, and Antimicrobial Properties." Inorganic Chemistry, 2016, 55: 5886-5894.

Kandel, S., et al., "Syntheses and X-ray crystal structures of a family of dinuclear silver(I) pyrazolates: Assessment of their antibacterial efficacy against P. aeruginosa with a soft tissue and skin infection model." Polyhedron, 2018, 154: 390-397.

* cited by examiner

R = Cl (1)
R = NO₂ (3)

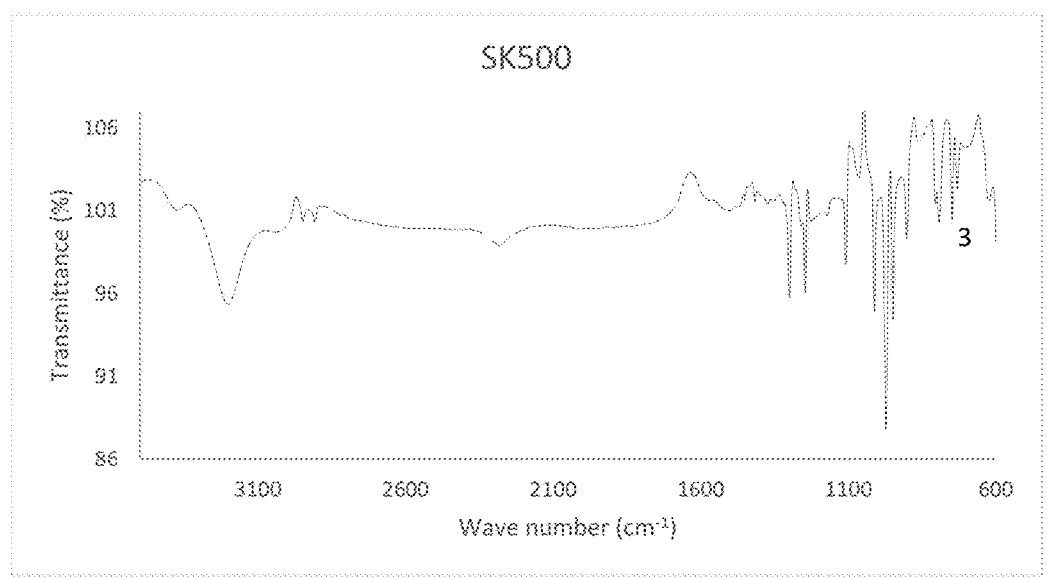
FIG. 23
FIG. 24A    FIG. 24B    FIG. 24C    FIG. 24D
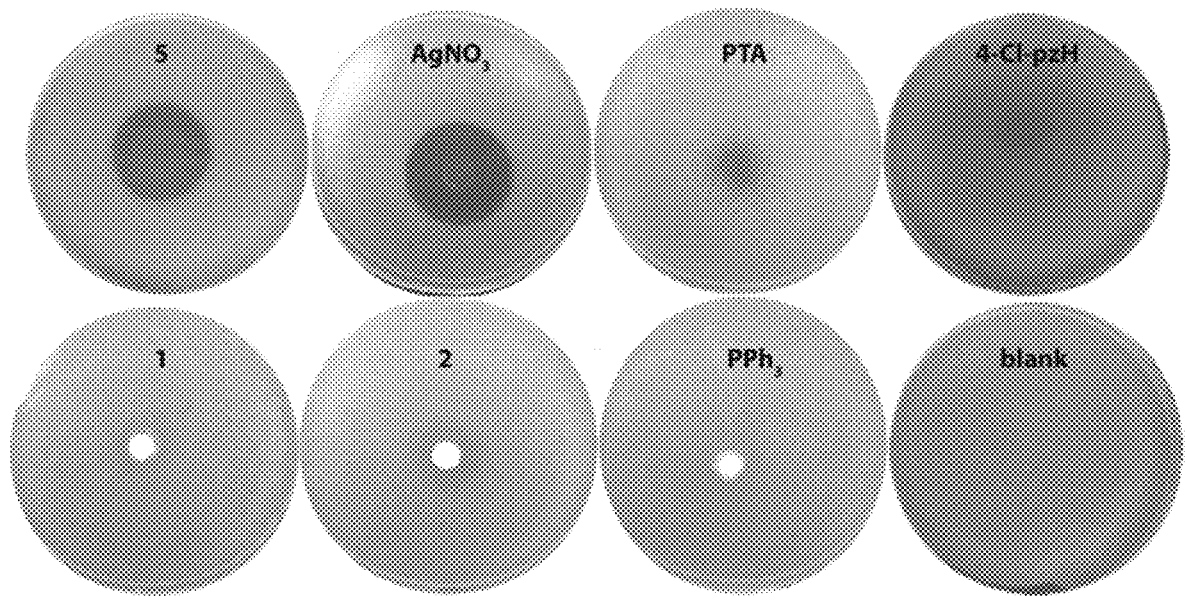
FIG. 24E    FIG. 24F    FIG.24G    FIG. 24H

SYNTHESIS AND ANTIMICROBIAL USES OF DINUCLEAR SILVER(I) PYRAZOLATES

CROSS-REFERENCE TO A RELATED APPLICATION

This application is a divisional application of co-pending application Ser. No. 17/513,990, filed Oct. 29, 2021; which is a continuation application of application Ser. No. 16/932,075, filed Jul. 17, 2020, now U.S. Pat. No. 11,160,829; which is a continuation of application Ser. No. 16/456,834, filed Jun. 28, 2019, now U.S. Pat. No. 10,828,327; which claims the benefit of U.S. provisional Application Ser. No. 62/722,664, filed Aug. 24, 2018, all of which are incorporated herein by reference in their entirety.

BACKGROUND OF THE INVENTION

Antibiotic resistance is currently an alarming issue and several health organizations throughout the World have already declared bacterial resistance towards antibiotics as "catastrophic". The Infectious Disease Society of America (IDSA) has expressed significant concern on antibacterial resistance, in particular regarding the multi-drug resistant bacteria (MDR), which have been singled out as an imminent threat to US public health. Among the Gram-positive variety, methicillin-resistant *Staphylococcus aureus* (MRSA) is annually responsible for more loss of life in US than the infectious HIV/AIDS disease. Gram-negative strains have also started showing resistance towards a range of antimicrobials. The notorious Gram-negative hospital infections are mostly caused by *Klebsiella pneumonia*, *Pseudomonas aeruginosa*, and *Acinetobacter baumannii*. These circumstances have prompted the research community in recent years to focus on developing alternative chemotherapeutics to combat antibacterial resistance.

Ionic or bioactive silver ($Ag^+$) has been found to be a quite effective antimicrobial against a broad range of microorganisms. Ionic Ag has been widely used in various commercially-available healthcare products and also as an antibacterial agent. Silver is "oligodynamic" because of its ability to exert its antimicrobial actions even at very low concentrations. In addition, $Ag^+$ ions interact with bacteria by several different mechanisms, making it difficult for the pathogens to develop resistance. In bacteria, $Ag^+$ ions interact with the nucleophilic amino acid residues, inhibit the function of oxidative enzymes, promote generation of reactive oxygen species (ROS) and interfere with DNA replication. These observations have led to silver-based antimicrobials, which are particularly effective against burn wound infections. For example, silver nitrate and silver sulfadiazine (SSD) are used extensively as topical antimicrobials for severe burn wounds. Slow and sustainable delivery of $Ag^+$ ions under a physiological milieu by dissociation of the topically applied compound is crucial to its effective antibacterial action, ensuring also that the Ag-based antimicrobial is not being over used, which might cause other undesirable side effects. Appropriately designed Ag(I) coordination complexes can meet these requirements.

Pyrazoles themselves have been reported to exhibit a wide range of biological activities, including antimicrobial, antifungal, anti-inflammatory, anti-convulsant, anticancer, and neuroprotective. Several pyrazole derivatives have already found their place in some clinically approved non-steroidal anti-inflammatory drugs (NSAIDs).

Many strains of bacteria spores (e.g., *Clostridium* species), Gram-positive bacteria (e.g., mycobacteria) and Gram-negative bacteria (e.g., *Pseudomonas aeruginosa* (*P. aeruginosa*)) have intrinsic resistance to antimicrobial agents. Moreover, many antimicrobial agents are not effective against biofilms. For example, *Serratia marcescens* (*S. marcescens*) and *Burkholderia cepacia* (*B. cepacia*) biofilms are found in disinfectant chlorhexidine solution, *P. aeruginosa* biofilm in iodophor antiseptics and on the interior surface of polyvinyl chloride pipes used in the production of providone-iodine antiseptics. Furthermore, overuse of these antimicrobial agents has led to drug resistance in microbes. Major concerns include cross-resistance and co-resistance with clinically used antimicrobial agents, which may present a potential public health risk.

Therefore, there exists a need for antimicrobials that are effective against a wide range of microbes, are not prone to induce microbial resistance, and provide antimicrobial activity in the context of biofilms.

BRIEF SUMMARY OF THE INVENTION

Provided herein are novel dinuclear silver (Ag) (I) pyrazolido complexes and methods of making and using them as antimicrobial agents. Advantageously, the novel dinuclear Ag(I) pyrazolido complexes have excellent antimicrobial effects when administered in vitro and in vivo. Further provided are methods of synthesizing the novel dinucelar Ag(I) pyrazolido complexes of the subject invention and methods of using them for the treatment of microbial infections in subjects in need of such treatment and for the growth inhibition and killing of microbes on surfaces or in compositions of matter such as food or cosmetics.

Advantageously, through introduction of specific ancillary ligands and the use of water soluble pyrazole, the dinuclear Ag(I) pyrazolido complexes of the subject invention can have excellent aqueous solubility, lipophilicity or both and can be used for excellent cellular uptake and in vitro and in vivo antimicrobial functionality.

BRIEF DESCRIPTION OF THE FIGURES

FIG. 1A shows a bis(3,4,5-R-pyrazolido)tetrakis(1,2-R)disilver(I) complex.

FIG. 1B shows a bis(3,4,5-R-pyrazolido)tetrakis(1,2-R; 1-R)disilver(I) complex. FIG. 1C shows a bis(3,4,5-R-pyrazolido)bis(1-R)disilver(I) complex.

FIG. 23 shows a IR spectrum for complex (5).

FIGS. 24A-24H show *Pseudomonas aeruginosa* lawns after 18 h incubation with pellets of 2% (w/w) of complex (5) (FIG. 24A), AgNO3 (FIG. 24B), PTA (FIG. 24C), 4-Cl-pzH (FIG. 24D), complex (1) (FIG. 24E), complex (2) (FIG. 24F), PPh3 (FIG. 24G) and blank plate (FIG. 24H).

FIG. 51A shows the optical density of *P. aeruginosa* treated with increasing concentrations of complex (5). FIG. 51B shows the optical density of *P. aeruginosa* treated with increasing concentrations of complex (29).

DETAILED DESCRIPTION OF THE INVENTION

Figure 1A:
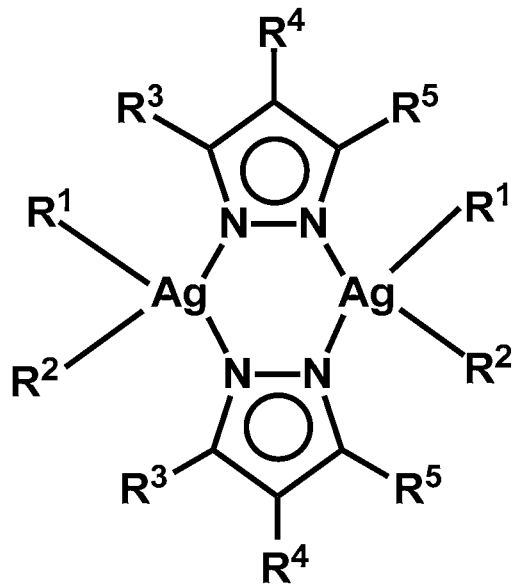
FIGS. 1A-1C show two general formulae of dinuclear silver (I) pyrazolido complexes of the invention.
Figure 1B:
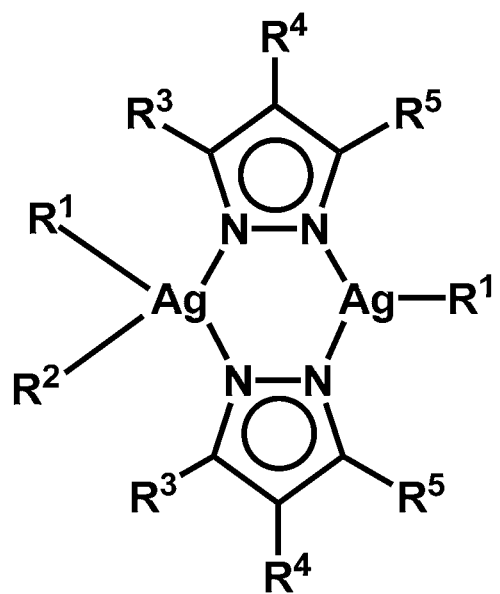
Figure 1C:
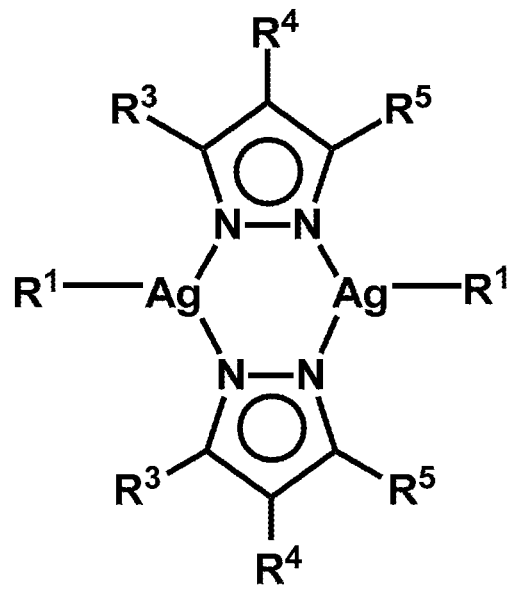
Figure 2A:
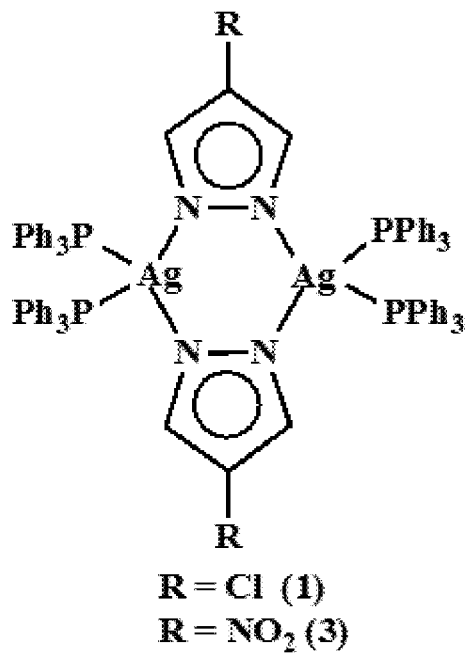
FIG. 2A shows a bis(μ-4-R-pyrazolido)tetrakis(PPh3)disilver(I) complex (1) where $R^3$ and $R^5$ are hydrogen and $R^4$=R=Cl and complex (3) when $R^4$=R=$NO_2$.
Figure 2B:
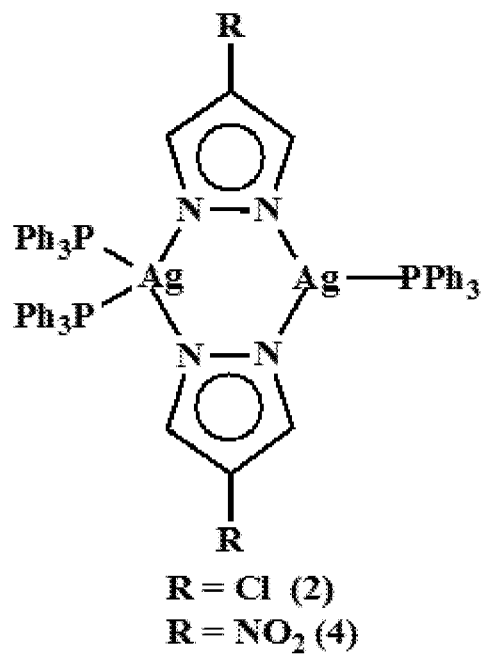
FIG. 2B shows a bis(μ-4-R-pyrazolido)tris(PPh3)disilver (I) complex (2) where $R^3$ and $R^5$ are hydrogen and $R^4$=R=Cl and complex (4) when $R^4$=R=$NO_2$.
Figure 2C:
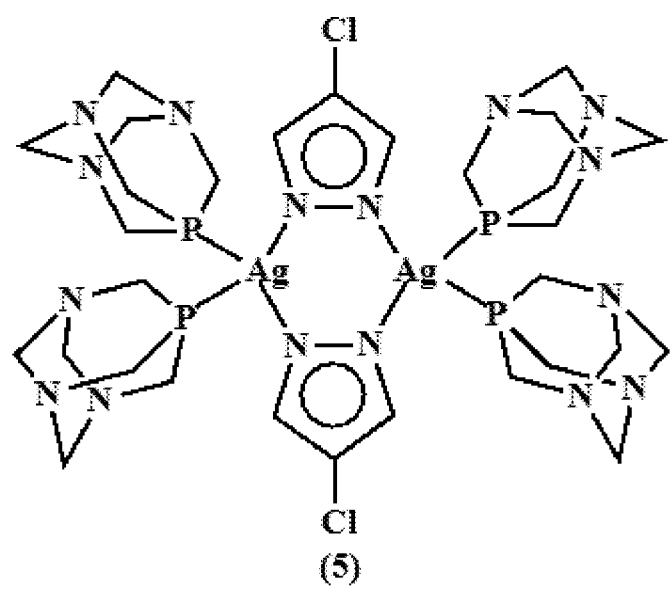
FIG. 2C shows a bis(μ-4-Cl-pyrazolido)tetrakis(PTA)disilver(I) complex (5).

Provided herein are compositions and methods of synthesis and use of novel Ag(I) pyrazolido complex-based antimicrobial compounds that are effective against a broad spectrum of bacteria, viruses, and fungi; do not induce microbial resistance; and provide anti-microbial activity even in the context of complex microbial structures, including biofilms.

The novel silver Ag(I) pyrazolido complexes of the subject invention enable slow and sustainable delivery of Ag$^+$ ions under physiological conditions and provide excellent antibacterial activity in vitro and in vivo with no inadvertent toxicity due to release of Ag+ under physiological conditions.

In some embodiments, the invention provides novel silver (I) pyrazolido complexes of the general formula of structure (A):

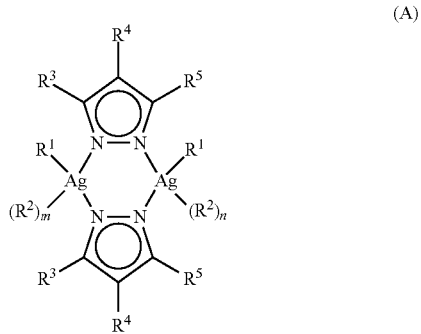

(A)

wherein $R^1$ and $R^2$ are each independently selected from the group consisting of 1,3,5-triaza-7-phosphaadamantane (PTA), phosphaadamantane (PA), $P(R')_3$, (4-sulfophenyl)diphenylphosphine (SDPP), phenanthrene diphenylphosphine (PDPP), 8-((4-phosphino)phenyl)-4,4-dimethyl-1,3,5,7-tetramethyl2,6-diethyl-4-bora-3a,4a-diaza-s-indacene (PMBODIPY), 8-((4-phosphino)phenyl)-4,4-diethyl-1,3,5,7-tetramethyl2,6-diethyl-4-bora-3a,4a-diaza-s-indacene(PEBODIPY), and 8-((4-phosphino)phenyl)-4,4-diphenyl-1,3,5,7-tetramethyl-2,6-diethyl-4-bora-3a,4a-diaza-s-indacene (PPBODIPY);

m is an integer selected from the group consisting of 0 and 1;

n is an integer selected from the group consisting of 0 and 1;

wherein $R^3$, $R^4$, and $R^5$ are independently selected from the group consisting of hydrogen, halogen, hydroxyl, nitro, alkyl, alkenyl, aryl, formyl, acetyl, hydroxyalkyl, halogen substituted alkyl, halogen substituted aryl, halogen substituted sulfuryl, imine-linked PTA, amine-linked PTA, imine-linked adamantane, amine-linked adamantine, imine-linked triphenylphosphine, and amine-linked triphenylphosphine; and each $R^6$ is independently selected from the group consisting of alkyl and aryl.

In some embodiments, the invention provides novel silver (I) pyrazolido complexes of the general formula of structure (C):

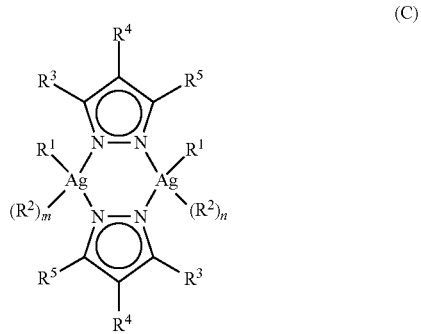

(C)

wherein $R^1$ and $R^2$ are each independently selected from the group consisting of 1,3,5-triaza-7-phosphaadamantane (PTA), phosphaadamantane (PA), $P(R^6)_3$, (4-sulfophenyl) diphenyl-phosphine (SDPP), phenanthrene diphenylphosphine (PDPP), 8-((4-phosphino)phenyl)-4,4-dimethyl-1,3,5,7-tetramethyl2,6-diethyl-4-bora-3a,4a-diaza-s-indacene (PMBODIPY), 8-((4-phosphino)phenyl)-4,4-diethyl-1,3,5,7-tetramethyl2,6-diethyl-4-bora-3a,4a-diaza-s-indacene (PEBODIPY), and 8-((4-phosphino)phenyl)-4,4-diphenyl-1,3,5,7-tetramethyl-2,6-diethyl-4-bora-3a,4a-diaza-s-indacene (PPBODIPY);

m is an integer selected from the group consisting of 0 and 1;

n is an integer selected from the group consisting of 0 and 1;

wherein $R^3$, $R^4$, and $R^5$ are independently selected from the group consisting of hydrogen, halogen, hydroxyl, nitro, alkyl, alkenyl, aryl, formyl, acetyl, hydroxyalkyl, halogen substituted alkyl, halogen substituted aryl, halogen substituted sulfuryl, imine-linked PTA, amine-linked PTA, imine-linked adamantane, amine-linked adamantine, imine-linked triphenylphosphine, and amine-linked triphenylphosphine; wherein each $R^6$ is independently selected from the group consisting of alkyl and aryl; or a pharmaceutically acceptable salt thereof.

In some embodiments, methods are provided that comprise reacting 4-Cl-pyrazole with silver benzoate (Ag (PhCOO)) in equimolar amounts of dry Tetrahydrofuran (THF) to generate insoluble $[Ag(4-Cl-pyrazolate)]_n$ polymers, which polymers are subsequently reacted with excess of triphenylphosphine ($PPh_3$) to generate the dimeric silver complex disilver(I)-bis(μ-4-Cl-pyrazolido)tetrakis($PPh_3$) (complex (1)).

In other embodiments, methods are provided that comprise reacting 4-Cl-pyrazole with silver benzoate (Ag (PhCOO)) in equimolar amounts of dry THF to generate insoluble $[Ag(4-Cl-pyrazolate)]_n$ polymers, which polymers are subsequently reacted with 1.5 equivalent of triphenylphosphine ($PPh_3$) to generate the dimeric silver complex disilver(I)-bis(μ-4-Cl-pyrazolido)($PPh_3$)$_3$ (complex (2)).

In further embodiments, methods are provided that comprise reacting 4-$NO_2$-pyrazole with silver benzoate to generate $[Ag(4-NO_2-pyrazolate)]\sim$ polymers that are subsequently reacted with excess of triphenylphosphine to generate the dimeric silver complex disilver(I)-bis(μ-4-$NO_2$-pyrazolido)tetrakis($PPh_3$) (complex (3)).

In yet other embodiments, methods are provided that comprise reacting 4-$NO_2$-pyrazole with silver benzoate to generate $[Ag(4-NO_2-pyrazolate)]_n$ polymers that are subsequently reacted with 1.5 equivalents of triphenylphosphine to generate the dimeric silver complex disilver(I)-bis(μ-4-$NO_2$-pyrazolido)($PPh_3$)$_3$]·$4H_2O$ (complex (4)).

In some embodiments, the methods of the subject invention comprise reacting 4-Cl-pyrazole with silver benzoate to generate insoluble $[Ag(4-Cl-pyrazolate)]_n$ polymers that are subsequently reacted with 4 equivalents of 1,3,5-triazaphosphaadamantane (PTA) to generate the dimeric silver complex disilver(I)-bis(μ-4-Cl-pyrazolido)tetrakis(PTA) (complex (5)).

In preferred embodiments, the methods of the subject invention comprise reacting 4-Cl-pyrazole with silver benzoate to generate insoluble $[Ag(4-Cl-pyrazolate)]\sim$ polymers that are subsequently reacted with 2 equivalents of 1,3,5-triazaphosphaadamantane (PTA) to generate the dimeric silver complex disilver(I)-bis(μ-4-chloride-pyrazolido)bis(PTA) (complex (28)).

In further preferred embodiments, the methods of the subject invention comprise reacting 3-Methyl-pyrazole with silver benzoate to generate insoluble [Ag(3-Me-pyrazolate)]~ polymers that are subsequently reacted with 2 equivalents of 1,3,5-triazaphosphaadamantane (PTA) to generate the dimeric silver complex disilver(I)-bis(μ-3-methyl-pyrazolido)bis(PTA) (complex (29)).

The symmetrical or unsymmetrical dinuclear Ag(I) pyrazolido complexes generated, according to the methods of the subject invention, have advantageous in vitro and in vivo functions including, but not limited to, antibacterial, antifungal, antiviral, anti-inflammatory, anti-convulsant, anticancer, neuroprotective, angiotensin converting enzyme (ACE) inhibitory, cholecystokinin-1 receptor antagonistic, and/or for estrogen receptor ligand activity.

The symmetrical dinuclear Ag(I) pyrazolido complexes can comprise two phosphine groups on each silver atom or, alternatively, can comprise one phosphine group on each silver atom.

The Ag(I) pyrazolido complexes, according to the subject invention, can be modified by introducing functional groups including, but not limited to, halogen, nitro, alkyl, alkenyl, aryl, formyl, acetyl, halogen substituted alkyl, and/or halogen substituted aryl in pyrazole positions 3-, 4-, and 5- to modulate aqueous solubility.

According to specific embodiments of the subject invention, the symmetrical and unsymmetrical Ag(I) pyrazolido complexes of the subject invention are further modified to enhance their aqueous solubility, lipophilicity, or both, by introducing appropriate ancillary groups.

In some embodiments, the dinuclear Ag(I) pyrazolido complexes are highly lipophilic.

In preferred embodiments, the dinuclear Ag(I) pyrazolido complexes of the subject invention are highly soluble in water. In more preferred embodiments, the dinuclear Ag(I) pyrazolido complexes of the subject invention possess optimal combinations of hydrophilic and lipophilic ligands to enable excellent cellular uptake and low toxicity.

An increased aqueous solubility can be imparted on the dinuclear Ag(I) pyrazolido complexes of the subject invention, using several strategies.

First, introduction of 1,3,5-triazaphosphaadamantane (PTA) ligands into the dinuclear Ag(I) pyrazolido complex, e.g., in complexes (5) and (6), results in substantially increased aqueous solubility due to strong H-bond interaction of the bridgehead N atoms with water molecules.

Second, increased aqueous solubility is accomplished by employing both water-soluble pyrazole derivatives and ancillary ligands. Examples of dinuclear Ag(I) pyrazolido complexes generated according to this strategy include, but are not limited to, complexes (8), (9), (10), (14), (15), and (16).

Third, increased aqueous solubility is accomplished by utilizing water-soluble pyrazole and highly lipophilic ancillary ligands. Examples of dinuclear Ag(I) pyrazolido complexes generated according to this strategy include, but are not limited to, complexes (11), (12), (13), and (17). Advantageously, it was found that the latter strategy providing Ag(I) pyrazolido complexes having an optimized combination of hydrophilic and lipophilic groups provide unexpected superior performance in vitro and in vivo. Without wanting to be bound by theory, it is indicated that the high physiological acceptability of such complexes combined with the optimal lipophilicity for improved cellular uptake causes their unexpected superior in vitro and in vivo performance.

In further embodiments, dinuclear Ag(I) pyrazolido complexes comprising an amine form of the pyrazole derivative are provided, which complexes also have high water solubility. Examples of such complexes include, but are not limited to, complexes (18), (19), (20), and (21).

Fluorescent reporter molecules, in general, allow the detection of the location of compounds comprising said reporters following in vitro and/or in vivo administration.

Also provided herein are fluorescent reporter-containing Ag(I) pyrazolido complexes and methods of synthesizing highly lipophilic biocompatible fluorescent reporter-containing dinuclear Ag(I) pyrazolido complexes including, but not limited to, complexes (22) and (23).

In preferred embodiments, methods are provided for synthesizing water soluble dinuclear Ag(I) pyrazolido complexes incorporating biocompatible fluorescent reporters, including, but not limited to, complexes (24), (25), (26), and (27). Advantageously, the complexes (24) to (27) provide unexpected superior performance in vitro and in vivo. Without wanting to be bound by theory, it is indicated that the superior functionality of complexes (24) to (27) is based on the optimized combination of hydrophilic and lipophilic groups providing high physiological acceptability of the complexes combined with the optimal lipophilicity for improved cellular uptake.

In preferred embodiments, methods are provided for making the dinuclear Ag(I) pyrazolido complexes of the subject invention by introducing ancillary ligands. In preferred embodiments, dinculear Ag(I) pyrazlido complexes are synthesized using [Ag$_2$O] (silver oxide), or [AgL] precursors, where L=CH$_3$COO, PhCOO, CF$_3$SO$_3$, NO$_3$, Cl (silver acetate, silver benzoate, silver trifluorosulfonate, silver nitrate, silver chloride, respectively). The pyrazole derivatives employed in the methods of the invention have different groups at the 3-, 4-, 5-positions, $R^3$, $R^4$, and $R^5$, which are independently selected from the group consisting of hydrogen, halogen, hydroxyl, nitro, alkyl, alkenyl, aryl, formyl, acetyl, hydroxyalkyl, halogen substituted alkyl, halogen substituted aryl, halogen substituted sulfuryl, imine-linked PTA, amine-linked PTA, imine-linked adamantane, amine-linked adamantine, imine-linked triphenylphosphine, and amine-linked triphenylphosphine.

Furthermore, the $R^1$ and $R^2$ groups of the pyrazole derivatives are independently selected from the group consisting of 1,3,5-triaza-7-phosphaadamantane (PTA), adamantane, phosphaadamantane (PA), P(R$^6$)$_3$, where the R$^6$ groups are selected from alkyl and aryl, (4-sulfophenyl)diphenylphosphine (SDPP), phenanthrene diphenylphosphine (PDPP), 8-((4-phosphino)phenyl)-4,4-dimethyl-1,3,5,7-tetramethyl-2,6-diethyl-4-bora-3a,4a-diaza-s-indacene (PMBODIPY), 8-((4-phosphino)phenyl)-4,4-diethyl-1,3,5,7-tetramethyl2, 6-diethyl-4-bora-3a,4a-diaza-s-indacene (PEBODIPY), and 8-((4-phosphino)phenyl)-4,4-diphenyl-1,3,5,7-tetramethyl-2,6-diethyl-4-bora-3a,4a-diaza-s-indacene: PPBODIPY.

The pyrazole derivatives are reacted with the silver precursors in equimolar ratio in dichloromethane or chloroform at ambient conditions to generate polymeric species with general formula, [Ag(pz*)]$_n$ (where pz*=differently substituted pyrazolido anions). Subsequently these polymeric compounds are reacted with phosphines, including but not limited to P(R$^6$)$_3$, where the R groups are selected from alkyl and aryl, PTA, PA, sulfophenyl)diphenylphosphine (SDPP), phenanthrene diphenylphosphine (PDPP), and/or a primary fluorescent phosphine BODIPY, including, but not limited to, PMBODIPY, PEBODIPY, and PPBODIPY to generate the desired dinuclear Ag(I) pyrazolido complexes of the invention.

For example, complex (5) of the subject invention comprising 1,3,5-triazaphosphaadamantane (PTA) as a co-ligand is highly water-soluble and provides unexpected superior antibacterial properties. Without wanting to be bound by theory it is submitted that by virtue of the ability of the PTA ligands of complex (5) of the invention to H-bond strongly with water molecules through the bridgehead N atoms, the dinucelar Ag(I) pyrazolido complex (5) of the invention is highly biocompatible and has minimal intrinsic toxicity.

Also provided are methods of synthesizing bis(μ-4-R-pyrazolido)tetrakis(1,3,5-triazaphosphaadamantane)disilver (I) complexes, e.g., of complex (6) wherein R can be H, Cl, or $NO_2$.

In some embodiments, methods are provided to synthesize bis(μ-4-R-pyrazolido)tetrakis(phosphaadamantane)disilver(I) complexes, e.g., of complex (7) wherein R can be H, Cl, or $NO_2$.

In some embodiments, methods are provided to synthesize bis(μ-4-1,3,5-triazaadamantane-imine-pyrazolido)tetrakis(1,3,5-triazaphosphaadamantane)disilver(I) complexes, e.g., of complex (8).

In some embodiments, methods are provided to synthesize bis(μ-4-hydroxyethyl-pyrazolido)tetrakis(1,3,5-triazaphosphaadamantane)disilver(I) complexes, e.g., of complex (9).

In some embodiments, methods are provided to synthesize bis(μ-4-sulfonylchloride-pyrazolido)tetrakis(1,3,5-triazaphosphaadamantane) disilver(I) complexes, e.g., complex (10).

In some embodiments, methods are provided to synthesize bis(μ-4-1,3,5-triazaadamantane-imine-pyrazolido)tetrakis(phosphaadamantane)disilver(I) complexes, e.g., complex (11).

In some embodiments, methods are provided to synthesize bis(μ-4-hydroxyethyl-pyrazolido)tetrakis(phosphaadamantane)disilver(I) complexes, e.g., complex (12).

In some embodiments, methods are provided to synthesize bis(μ-4-sulfonylchloride-pyrazolido)tetrakis(phosphaadamantane)disilver(I) complexes, e.g., complex (13).

In some embodiments, methods are provided to synthesize bis(μ-4-1,3,5-triazaadamantane-imine-pyrazolido)tetrakis((4-sulfophenyl)-diphenylphosphine)disilver(I) complexes, e.g., complex (14).

In some embodiments, methods are provided to synthesize bis(μ-4-hydroxyethyl-pyrazolido)tetrakis((4-sulfophenyl)-diphenylphosphine)disilver(I) complexes, e.g., complex (15).

In some embodiments, methods are provided to synthesize bis(μ-4-sulfonylchloride-pyrazolido)tetrakis((4-sulfophenyl)-diphenylphosphine)disilver(I) complexes, e.g., complex (16).

In some embodiments, methods are provided to synthesize bis(μ-4-adamantane-imine-pyrazolido)tetrakis((4-sulfophenyl)-diphenylphosphine)disilver(I) complexes, e.g., complex (17).

In some embodiments, methods are provided to synthesize bis(μ-4-1,3,5,-triazaadamantane-amine-pyrazolido)tetrakis(PTA)disilver(I) complexes, e.g., complex (18).

In some embodiments, methods are provided to synthesize bis(μ-4-1,3,5-triazaadamantane-amine-pyrazolido)tetrakis(phosphaadamantane)disilver(I)complexes, e.g., complex (19).

In some embodiments, methods are provided to synthesize bis(μ-4-1,3,5-triazaadamantane-amine-pyrazolido)tetrakis((4-sulfophenyl)diphenylphosphine)disilver(I) complexes, e.g., complex (20).

In some embodiments, methods are provided to synthesize bis(μ-4-adamantane-amine-pyrazolido)tetrakis((4-sulfophenyl)diphenylphosphine)disilver(I) complexes, e.g., complex (21).

In some embodiments, methods are provided to synthesize bis(μ-4-R-pyrazolido) tetrakis(8-((4-phosphino)phenyl)-4,4-dimethyl-1,3,5,7-tetramethyl-2,6-diethyl-4-bora-3a,4a-diaza-s-indacene)disilver(I) complexes, e.g., complex (22) wherein R can be H, Cl, or $NO_2$.

In some embodiments, methods are provided to synthesize bis(μ-4-R-pyrazolido)tetrakis(phenanthrene-diphenylphosphine)disilver(I) complex (23) wherein R can be H, Cl, or $NO_2$.

In some embodiments, methods are provided to synthesize bis(μ-4-1,3,5-triazaadamantane-imine-pyrazolido) tetrakis(8-((4-phosphino)phenyl)-4,4-dimethyl-1,3,5,7-tetramethyl-2,6-diethyl-4-bora-3a,4a-diaza-s-indacene)disilver(I) complexes, e.g., complex (24).

In some embodiments, methods are provided to synthesize bis(μ-4-1,3,5-triazaadamantane-amine-pyrazolido)tetrakis(8-((4-phosphino)phenyl)-4,4-dimethyl-1,3,5,7-tetramethyl-2,6-diethyl-4-bora-3a,4a-diaza-s-indacene)disilver(I) complexes, e.g., complex (25).

In some embodiments, methods are provided to synthesize bis(μ-4-hydroxyethyl-pyrazolido)tetrakis(8-((4-phosphino)phenyl)-4,4-dimethyl-1,3,5,7-tetramethyl-2,6-diethyl-4-bora-3a,4a-diaza-s-indacene)disilver(I) complexes, e.g., complex (26).

In some embodiments, methods are provided to synthesize bis(μ-4-sulfonylchloride-pyrazolido)tetrakis(8-((4-phosphino)phenyl)-4,4-dimethyl-1,3,5,7-tetramethyl-2,6-diethyl-4-bora-3a,4a-diaza-s-indacene)disilver (I) complexes, e.g., complex (27).

In some embodiments, methods are provided to synthesize bis(μ-4-chloride-pyrazolido)bis(1,3,5-triazaphosphaadamantane)disilver(I) complexes, e.g., complex (28).

In some embodiments, methods are provided to synthesize bis(μ-3-methyl-pyrazolido)bis(1,3,5-triazaphosphaadamantane)disilver(I) complexes, e.g., complex (29).

Also provided are methods of using compositions, such methods can comprise treating bacterial infections in subjects in need of such treatment. For example, the methods of treating a subject at risk of, or having, a bacterial, fungal infection, and/or viral infection comprise administering to the subject a composition according to the subject invention, which composition comprises a dinuclear silver(I) pyrazolido complex of the invention.

Further provided are methods of killing microbes and/or inhibiting their growth, the method comprising contacting the microbes with a composition according to the subject invention, which composition comprises a dinuclear silver(I) pyrazolido complex of the invention.

For example, in a preferred embodiment, using a composition comprising complex (5), an unexpected antibacterial effect against the Gram-negative bacterial strain *P. aeruginosa* was observed.

In further embodiments, it was surprisingly determined that a composition comprising complex (29) resulted in a significant antibacterial effect against the Gram-negative bacterial strain *P. aeruginosa*, which antibacterial effect was significantly higher than the antibacterial effect of a composition comprising, e.g., complex (5).

In some embodiments of the subject invention, the Ag(I) pyrazolido complexes provided are highly active against Gram-positive microbes (e.g., *S. aureus*), Gram-negative microbes (e.g., *Escherichia coli* (*E. coli*), *P. aeruginosa*), fungi (e.g., *C. albicans*), and viruses and can be used in methods of treating subjects suffering from such Gram-positive, Gam-negative, fungal, and viral infections.

Advantageously, the Ag(I) pyrazolido complexes of the subject invention are biocompatible, non-hemolytic, and non-cytotoxic at concentrations above the minimum inhibitory concentration (MIC), and are therefore attractive for a wide range of consumer products such as, for example, cosmetics, skin lotions or creams, antibiotic drugs, food preservatives, surface cleaners, antiseptic agents, and/or wound care products. The compositions can also be used to control plant and animal pathogens. A "biocompatible" material is defined herein as a material capable of performing with an appropriate host response in a specific application.

Minimum inhibitory concentration (MIC) is defined as the minimum concentration of a composition required to inhibit growth of a given microbe for an 18 hour period (bacteria) or 42 hour period (fungi, viruses). A MIC less than 1 mM is desirable. Even more desirable is a MIC of 10 µM or less. A lower MIC indicates higher antimicrobial activity.

Minimum bactericidal concentration (MBC) is defined as the minimum concentration of a composition required in order to kill a given microbe. A lower MBC indicates higher antimicrobial activity.

The complexes of the subject invention can have a minimum inhibitory concentration (MIC) of about 100 mM to about 0.1 nM and preferably about 10 mM to about 0.1 nM, and more preferably 1 µM to about 0.1 nM against a bacterium. In a specific embodiment, the complexes can have a MIC of about 5 µM to about 5 nM against *P. aeruginosa*.

Non-limiting exemplary bacteria that can be inhibited or killed with Ag(I) pyrazolido complexes, according to the subject invention, include, but are not limited to Gram-positive *Staphylococcus aureus* (*S. aureus*), Gram-negative *Escherichia coli* (*E. coli*), fungus *Candida albicans* (*C. albicans*) and other yeasts and Gram-negative *Pseudomonas aeruginosa* (*P. aeruginosa*). Other microbes include Gram-positive *Staphylococcus epidermidis* (*S. epidermidis*), Gram-positive Methicillin-resistant *Staphylococcus aureus* (MRSA), Gram-positive Vancomycin-resistant *Enterococcus* (VRE), Gram-negative *Acinetobacter baumannii* (*A. baumannii*), Gram-negative *Klebsiella pneumoniae* (*K pneumoniae*) and the fungus *Cryptococcus neoformans* (*C. neoformans*).

Further Gram-positive bacteria to be treated according to the subject invention include, but are not limited to, *Actinomyces, Arthrobacter, Bifidobacterium, Corynebacteruim, Frankia, Micrococcus, Micromonospora, Mycobacterium, Nocardia, Propionibacterium, Streptomyces, Bacillus, Listeria, Staphylococcus, Enterococcus, Lactobacillus, Lactococcus, Leuconostoc, Pediococcus, Streptococcus, Acetobacterium, Clostridium, Eubacterium, Heliobacterium, Megasphaera, Pectinatus*, Selenormonas, *Zymophilus, Sporomusa, Mycoplasma, Spiroplasma, Ureaplasma*, and *Erysipelothrix*.

Further Gram-negative bacteria to be treated according to the subject invention include, but are not limited to, *Acinetobacter, Actinobacillus, Bordetella, Brucella, Campylobacter, Cyanobacteria, Enterobacter, Erwinia, Escherichia coli, franciscella, Helicobacter, Hemophilus, Klebsiella, Legionella, Moraxella, Neisseria, Pasteurella, Proteus, Pseudomonas, Salmonella, Serratia, Shigella, Treponema, Vibrio*, and *Yersinia*.

Further fungi to be treated according to the subject invention include, but are not limited to, *Coccidioides, Cryptococcus gatii, Pneumocystis jirovecii, Sporothrix, Blastomyces, Cryptococcus neofromans, Histoplasma, Talaromyces*, and Tinea corporis.

Furthermore, viruses to be treated according to the subject invention, include, but are not limited to, Herpes simplex virus type 1 and 2, Human Immunodeficiency Virus (HIV), Hepatitis B virus, Hepatitis C virus, Rhinovirus, Influenza virus, Variola virus, Human enterovirus C, Cowpox virus, Respiratory syncytial virus, Paramyxoviridiae, Poxviridae, and Picornaviridae.

The Ag(I) pyrazolido complexes, according to the subject invention, can be provided separately or in combination as medicaments that are antibacterial, antiviral, antifungal, or any combination thereof. The medicaments can be formulated according to known methods for preparing pharmaceutically useful compositions. Such pharmaceutical compositions can be adapted for various forms of administration, such as, but not limited to, oral, parenteral, intravenous, nasal, topical, pulmonary, and transdermal. The Ag(I) pyrazolido complexes, according to the subject invention, can be provided as solutions, amorphous compounds, injectables, pills, inhalants, or in any other form for administration. The compositions comprising Ag(I) pyrazolido complexes of the subject invention can include pharmaceutically acceptable carriers or diluents. Formulations are described in a number of sources, which are well known and readily available to those skilled in the art. For example, *Remington's Pharmaceutical Science* (Martin EW [1995] Easton Pennsylvania, Mack Publishing Company, $19^{th}$ ed.) describes formulations that can be used in connection with embodiments of the invention.

Formulations suitable for administration include, e.g., aqueous sterile injection solutions, which may contain antioxidants, buffers, bacteriostats, and solutes, which render the formulation isotonic with the blood of the intended recipient; and aqueous and nonaqueous sterile suspensions, which may include suspending agents and thickening agents.

The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, or tablets of the Ag(I) pyrazolido complex comprising compositions. It should be understood that in addition to the ingredients particularly mentioned above, the formulations of the subject invention can include other agents conventional in the art having regard to the type of formulation in question.

Pharmaceutically acceptable carriers used in Ag(I) pyrazolido complex formulations according to the subject invention include, but are not limited to, inert diluents and vehicles such as: one or more excipients, buccal tablets, troches, capsules, elixirs, suspensions, syrups, wafers, and aerosol sprays. Tablets, troches, pills, capsules, and the like may, but do not necessarily, contain binders, such as gum tragacanth, acacia, corn starch or gelatin; excipients, such as dicalcium phosphate; disintegrating agents, such as corn starch, potato starch, or alginic acid; lubricants, such as magnesium stearate; sweetening agents, such as sucrose, fructose, lactose or aspartame; flavoring agents, such as peppermint, oil of wintergreen, or cherry flavoring; liquid carriers, such as a vegetable oil or a polyethylene glycol; and/or solid carriers; such as finely divided solids such as talc, clay, microcrystalline cellulose, silica, or alumina. Any material used in preparing the dosage form should be pharmaceutically acceptable and substantially non-toxic in the amounts employed. The dosage form may be a sustained-release preparation. Other dosage forms can include surfactants or other adjuvants. Liquid compositions for topical use can be applied from absorbent pads or be impregnated on bandages and other dressings. Thickeners, such as synthetic polymers, fatty acids, fatty acid salts and esters, fatty alcohols, modified celluloses or modified mineral materials, can be employed with liquid carriers.

Ag(I) pyrazolido complexes may be in the free base form or in the form of an acid salt thereof. In some embodiments, compounds as described herein may be in the form of a pharmaceutically acceptable salt, which are known in the art (Berge S. M. et al., *J. Pharm. Sci.* (1977) 66(1):1-19). Pharmaceutically acceptable salts as used herein include, for example, salts that have the desired pharmacological activity of the parent compound (salts which retain the biological effectiveness and/or properties of the parent compound and which are not biologically and/or otherwise undesirable). The acid salts can be generated with any pharmaceutically acceptable organic or inorganic acid.

Pharmaceutically acceptable salts may be derived from, e.g., and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Salts, as described herein, may be prepared by conventional processes known to a person skilled in the art, for example, and without limitation, by combining the free form with an organic acid or cation exchange from other salts. Those skilled in the art will appreciate that preparation of salts may occur in situ during isolation and purification of the compounds or preparation of salts may occur by separately reacting an isolated and purified compound.

Silver(I) pyrazolido complexes or pharmaceutical compositions for use as described herein may be administered by means of a medical device or appliance such as an implant, graft, prosthesis, stent, etc. Also, implants may be devised that are intended to contain and release such compounds or compositions. An example would be an implant made of a polymeric material adapted as a vehicle to release the Ag(I) pyrazolido complexes over a period of time.

An "effective amount" of a Ag(I) pyrazolido complex comprising pharmaceutical composition includes a therapeutically effective amount or a prophylactically effective amount. A "therapeutically effective amount" refers to an amount effective, at dosages and for periods of time necessary, to achieve the desired therapeutic result. A therapeutically effective amount of a Ag(I) pyrazolido complex formulation may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects.

A "prophylactically effective amount" refers to an amount effective, at dosages and for periods of time necessary, to achieve the desired prophylactic result. Typically, a prophylactic dose is used in subjects prior to the disease, so that a prophylactically effective amount may be less than a therapeutically effective amount.

Dosage values may vary with the severity of the condition to be alleviated. For any particular subject, specific dosage regimens may be adjusted over time according to the individual need and the professional judgment of the person administering or supervising the administration of the compositions. Dosage ranges suggested herein are exemplary only and do not limit the dosage ranges that may be selected by medical practitioners. The amount of Ag(I) pyrazolido complexes in the composition may vary according to factors such as the disease state, age, sex, and weight of the subject. Dosage regimens may be adjusted to provide the optimum therapeutic response.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Materials and Methods

Reagent grade chemicals were purchased from Aldrich Chemical Co, Alfa Aesar, Fisher scientific and Acros Organics. THF was distilled over Na/benzophenone and $CH_2Cl_2$ was distilled over $CaCl_2$/$CaH_2$ prior to use. NMR spectra were recorded on 400 MHz or 500 MHz Bruker Avance spectrometers. FT-IR spectra were recorded with a Perkin Elmer Spectrum 100 FT-IR Spectrometer. Elemental analyses (CHN) were performed by Galbraith Laboratories, Inc. at Knoxville, TN. The detail procedures for preparations of all complexes are included in the Supplementary Information. The IR and $^1H$ NMR spectra of some of the complexes have also been provided.

Example 1—Synthesis and Structures of the Complexes

Reaction of 4-R-pzH (where R=Cl and $NO_2$ and pzH=pyrazole) with silver benzoate in equimolar amounts in dry THF at room temperature uniformly resulted in insoluble polymers, $[Ag(R\text{-}pz)]_n$. These polymeric complexes were isolated and suspended in $CH_2Cl_2$ solution and reaction with appropriate phosphines ($PPh_3$ and PTA) at ambient temperature resulted in the corresponding dimeric silver complexes (1) to (5). Depending on the amount of the phosphine used in these reactions, either symmetrical or unsymmetrical dinuclear complexes were isolated. For example, when $[Ag(R\text{-}pz)]_n$ polymers were reacted with 1.5 equivalents per Ag atom of, e.g., triphenylphosphine ($PPh_3$) or 1.5 equivalents per Ag atom of PTA, dimeric silver complexes were generated with two $PPh_3$ groups on a first silver atom and one $PPH_3$ group on a second silver atom or, with two PTA groups on a first silver atom and one PTA group on a second silver atom.

When [Ag(R-pz)]$_n$ polymers were reacted with 1 equivalent per Ag atom of, e.g., triphenylphosphine (PPh$_3$) or 1 equivalent per Ag atom of PTA, dimeric silver complexes were generated with one PPh$_3$ group on each first and second silver atom or one PTA on each first and second silver atom.

When [Ag(R-pz)]$_n$ polymers were reacted with 2 equivalents per Ag atom of, e.g., triphenylphosphine (PPh$_3$) or 2 equivalents per Ag atom of PTA, dimeric silver complexes were generated with two PPh$_3$ groups on each first and second silver atom or two PTA groups on each first and second silver atom.

All complexes provided herein were neutral and soluble in variety of organic solvents. Moreover, complex (5) was also highly soluble in aqueous media, see: S. Kandel, J. Stenger-Smith, I. Chakraborty, R. G. Raptis, Syntheses and X-ray crystal structures of a family of dinuclear silver(I) pyrazolates: Assessment of their antibacterial efficacy against *P. aeruginosa* with a soft tissue and skin infection model, Polyhedron (2018) 154, 390-397, (doi: https://doi.org/l0.1016/j.poly.2018.08.015) incorporated herewith in its entirety.

Further complexes, according to the subject invention, synthesized using [Ag$_2$O] (silver oxide), or [AgL] precursors, where L=CH$_3$COO, PhCOO, CF$_3$SO$_3$, NO$_3$, Cl (silver acetate, silver benzoate, silver trifluorosulfonate, silver nitrate, silver chloride, respectively).

Three pyrazole derivatives with different groups at 3-, 4-, 5-positions (R$^3$, R$^4$, and R$^5$, respectively, see Structure B below, were employed. Reactions of these pyrazoles with the silver precursors in 1, 1.5, or 2 equivalents in dichloromethane or chloroform at ambient conditions furnish polymeric species with general formula, [Ag(pz*)]$_n$ (where pz*=differently substituted pyrazoles). The subsequent reactions of these polymeric compounds with appropriate tertiary phosphines P(R$^6$)$_3$, where the R$^6$ groups are selected from alkyl and aryl, PTA, PA, SDPP, PDPP, and/or a primary fluorescent phosphine BODIPY PMBODIPY, PEBODIPY, and PPBODIPY generated the desired complexes.

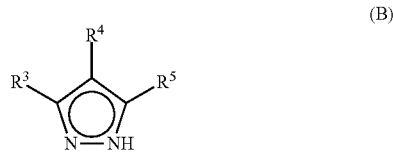

(B)

wherein R$^3$, R$^4$, and R$^5$ are independently selected from the group consisting of halogen, hydroxyl, nitro, alkyl, alkenyl, aryl, formyl, acetyl, hydroxyalkyl, halogen substituted alkyl, halogen substituted aryl, halogen substituted sulfuryl, imine-linked PTA, amine-linked PTA, imine-linked adamantane, amine-linked adamantine, imine-linked triphenylphosphine, and amine-linked triphenylphosphine; and each R$^6$ is independently selected from the group consisting of alkyl and aryl.

Example 2—Synthesis of [Ag$_2$(4-Cl-Pz)$_2$(Pph$_3$)$_4$] Complex (1)

Amounts of 10.3 mg (0.101 mmol) 4-Cl-pzH and 22.9 mg (0.10 mmol) Ag(PhCOO) were added to 5 mL THF and the reaction mixture was stirred at room temperature for 12 h. After this time, the mixture was filtered and the insoluble polymeric [Ag(4-Cl-pz)]$_n$ was collected by filtration and was thoroughly washed with CH$_2$Cl$_2$ to remove any unreacted starting materials. The solid was then dried under vacuum (Yield, 19.5 mg (93%), based on Ag(PhCOO) as a limiting reagent). Subsequently, 19.5 mg (0.093 mmol) of the dry solid was suspended in 5 mL CH$_2$Cl$_2$, 131 mg PPh$_3$ (0.50 mmol) was added and the reaction mixture was stirred at room temperature for 20 min resulting in a clear colorless solution. The solvent was removed under reduced pressure and the resulting solid was thoroughly washed with hexanes to eliminate any excess PPh$_3$. Finally the solid material was dissolved in CH$_2$Cl$_2$ and carefully layered with hexanes. X-ray quality block-shaped colorless crystals of (1). Yield: 60 mg (88%). Anal. Calcd for C$_{78}$H$_{64}$N$_4$Cl$_2$P$_4$Ag$_2$ (1467.93 g mol$^{-1}$): C, 62.82; H, 4.39; N, 3.82. Found: C, 62.73; H, 4.60; N, 3.51. IR ($v_{max}$, cm$^{-1}$): 3046(w), 1477(m), 1432(s), 1268(w), 1174(w), 1093(m), 1024(m), 952(m), 815(w), 742(s), 692(s), 615(w). $^1$H NMR (400 MHz, CDCl$_3$) δ (ppm): 7.55 (s, 4H, —CH/pz), 7.69-7.32 (m, 60H, —CH/PPh$_3$). 31P NMR (12.35 MHz, CDCl$_3$, ppm): −30.03 (PPh$_3$ at −5.89 ppm as reference).

Example 3—Synthesis of [Ag$_2$(4-Cl-Pz)$_2$(Pph$_3$)$_3$] Complex (2)

The [Ag$_2$(4-Cl-pz)$_2$(PPh$_3$)$_3$] (2) complex was synthesized in the same way as complex 1, except 1.5 equivalents of PPh$_3$ was used in this reaction. The solid obtained from the colorless reaction solution was washed thoroughly with hexanes and dried under vacuum. Next, this solid was dissolved in CH$_2$Cl$_2$ and layered with hexanes. Single crystals (as colorless blocks) of complex 2 were obtained after one week. Yield: 52 mg (92%). Anal. Calcd for C$_{60}$H$_{49}$N$_4$Cl$_2$P$_3$Ag$_2$ (1205.64 g mol$^{-1}$): C, 59.77; H, 4.10; N, 4.65. Found: C, 59.29; H, 3.99; N, 4.56. IR ($v_{max}$, cm$^{-1}$) 3048(w), 1477(m), 1432(s), 1268(w), 1174(w), 1093(m), 1024(m), 952(m), 817(w), 744(s), 692(s), 615(w). $^1$H NMR (400 MHz, CDCl$_3$) δ (ppm): 7.41 (s, 4H, —CH/pz), 7.39-7.27 (m, 45H, —CH/PPh$_3$). $^{31}$P NMR (CDCl$_3$, ppm): −27.82 (PPh$_3$ as reference).

Example 4—Synthesis of [Ag$_2$(4-NO$_2$-Pz)$_2$(Pph$_3$)$_4$] Complex (3)

The [Ag$_2$(4-NO$_2$-pz)$_2$(PPh$_3$)$_4$] (3) complex was prepared by the same procedure as complex (1), using [Ag(4-NO$_2$-pz)]$_n$ polymeric precursor (this polymer was obtained from the reaction of Ag(PhCOO) and 4-NO$_2$-pzH following the same reaction conditions employed to isolate [Ag(4-Cl-pz)]$_n$ polymer) and excess PPh$_3$. Yield: 58 mg (88%). Anal. Calcd for C$_{78}$H$_{64}$N$_6$O$_4$P$_4$Ag$_2$ (1489.04 g mol$^{-1}$): C, 62.92; H, 4.33; N, 5.64. Found: C, 61.90; H, 4.28; N, 5.66. IR ($v_{max}$, cm$^{-1}$): 3050(w), 1496(m), 1475(s), 1430(m), 1392(s), 1259(s), 1147(m), 1089(m), 1002(m), 852(w), 811(w), 742(s), 690(s), 601(s)). $^1$H NMR (400 MHz, CDCl$_3$) δ (ppm): 7.91 (s, 4H, —CH/pz), 7.70-7.24 (m, 60H, —CH/PPh$_3$). $^{31}$P NMR (CDCl$_3$, ppm): −29.40 (PPh$_3$ as reference.

Example 5—Synthesis of [Ag$_2$(4-NO$_2$-Pz)$_2$(Pph$_3$)$_3$]·4H$_2$O Complex (4)·4H$_2$O The [Ag$_2$(4-NO$_2$-pz)$_2$(PPh$_3$)$_3$]·4H$_2$O (4)·4H$_2$O complex was prepared by the same procedure as complex (2), using [Ag(4-NO$_2$-pz)]$_n$ polymeric precursor and 1.5 equivalent of PPh$_3$. Yield: 52 mg (94%). Anal. Calcd for C$_{60}$H$_{49}$N$_6$O$_4$P$_3$Ag$_2$ (1298.70 g mol$^{-1}$): C, 55.44; H, 4.39; N, 6.46. Found: C, 56.22; H, 4.29; N, 6.28. IR ($v_{max}$, cm$^{-1}$): 3050(w), 1479(s), 1432(m), 1396(s), 1263(s), 1151(m), 1093(m), 1002(m), 854(w), 811(m), 742(s), 692(s), 603(s).

$^1$H NMR (400 MHz, CDCl$_3$) δ (ppm): 7.81 (s, 4H, —CH/pz), 7.38-7.22 (m, 45H, —CH/PPh$_3$). $^{31}$P NMR (CDCl$_3$, ppm): −27.31 (PPh$_3$ as reference).

Example 6—Synthesis of [Ag$_2$(4-Cl-Pz)$_2$(PTA)$_4$] PTA Complex (5)

PTA is an attractive auxiliary ligand for various catalytic reactions. PTA is highly biocompatible, has minimal intrinsic toxicity [29], and has been utilized in the development of transition metal-based anticancer agents with excellent anti-angiogenic and anti-metastatic properties. The [Ag$_2$(4-Cl-pz)$_2$(PTA)$_4$] PTA (5) complex was prepared by the same procedure as complex (1), using [Ag(4-Cl-pz)]$_n$ polymeric precursor and 4 equivalents of PTA. 10.3 mg (0.101 mmol) 4-Cl-pzH and 22.9 mg (0.1 mmol) Ag(PhCOO) were added to 5 mL THF and the reaction mixture was stirred at room temperature for 12 h. After this time, the mixture was filtered and the insoluble polymeric [Ag(4-Cl-pz)]$_n$ was collected by filtration and was thoroughly washed with CH$_2$Cl$_2$ to remove any unreacted starting materials. The solid was then dried under vacuum (Yield, 19.5 mg (93%), based on Ag(PhCOO) as a limiting reagent). Subsequently, 19.5 mg (0.093 mmol) of the dry solid was suspended in 5 mL CH2Cl2, 58.5 mg PPTA (0.372 mmol) was added and the reaction mixture was stirred at room temperature for 2 minutes resulting in a clear colorless solution. Finally, it was allowed to air concentration. X-ray quality block-shaped colorless crystals of 1. Yield: 25 mg (51%). Anal. Calcd. for C$_{36}$H$_{64}$N$_{19}$Cl$_2$P$_5$Ag$_2$ (1787.17 g mol$^{−1}$): C, 35.90; H, 5.36; N, 22.09. Found: C, 36.51; H, 6.04; N, 21.10. IR ($v_{max}$, cm$^1$): 3197(s), 2944(w), 2906(w), 2275(w), 1637(w), 1448 (m), 1411(s), 1295(s), 1241(s), 1105(m), 1037(s), 1012(s), 970(s), 948(m), 900(s), 794(m). $^1$H NMR (400 MHz, D$_2$O) d (ppm): 7.67 (s, 4H, —CH/pz), 4.23-3.32 (m, 48H, —CH/PPh$_3$). $^{31}$P NMR (D$_2$O, ppm): −178.31 (PTA at −98.51 ppm as reference).

Example 7—Packing Patterns

Analysis of the packing patterns for all five complexes reveals no classical hydrogen bonding interactions. In case of both (1) and (5), a relatively weak C—H—Cl intermolecular interactions (with C—Cl, 3.580(5) A, symmetry code: x+1, y, z+1 for (1) and C—Cl, 3.501(4) Å, symmetry code: x−½, −y+½, z+½ for (5) consolidated their extended structures.

In case of both (3) and (4), a relatively weak C—H—O intermolecular interactions (with C—O, 3.222(12) A, symmetry code: x−1, y, z−1 and C—O, 3.329(10) A, symmetry code: −x+1, −y+1, −z+I for (3) and C—O, 3.461(6) A, symmetry code: −x+1, −y, −z+1 for (4) consolidated their extended structures.

Example 8—X-Ray Data Collection and Structure Refinement

Colorless block-shaped crystals of complexes (1) to (5) were obtained by recrystallization through diffusion of hexanes into their dichloromethane (CH$_2$Cl$_2$) solutions. In all cases a suitable crystal was selected and mounted on a Bruker D8 Quest diffractometer equipped with PHOTON 100 detector operating at T=298 K. Data were collected with w shutter less scan technique using graphite monochromated Mo-Kα radiation (λ=0.71073 Å). The total number of runs and images for data collection was based on strategy calculation from the program APEX3 (Bruker) [36]. Resolution of θ>26° was achieved in all cases. Cell parameters were retrieved using the SAINT (Bruker) software [37] and refined using SAINT (Bruker) on 9960 reflections for complexes (1) and (2), 9056 reflections for complex (3), 9879 reflections for complex (4) and 9926 reflections for complex (5). Data reduction was performed using the SAINT (Bruker) software, which corrects for Lorentz and polarization effects. The final completeness was 95.3% for complex (1), 99.7% for complex (2), 99.6% for complex (3), 99.4% for complex (4) and 99.2% for complex (5). Multi-scan absorption corrections were performed on all data sets using SADABS 2016/2. The minimum and maximum transmissions for complex (1) were 0.685 and 0.746, for complex (2) were 0.695 and 0.745, for complex (3) were 0.646 and 0.745, for complex (4) were 0.685 and 0.745 and for complex (5) were 0.646 and 0.745 respectively. The structures for complexes (1) to (4) were solved in the space group P-1 (No. 2) and for complex (5) in C2/c (No. 15) by intrinsic phasing using the SheLXT structure solution program and refined by full matrix least square procedure on F$^2$ using version 2016/6 of SheLXL. The non-hydrogen atoms were refined anisotropically in all cases. Hydrogen atom positions were calculated geometrically and refined using the riding model. For structures of complexes (1), (3) and (5) only half of the molecule is present in the asymmetric unit, with the other half consisting of symmetry equivalent atoms.

To alleviate the complications related to solvent accessible voids within the extended lattice of complex (2), the SQUEEZE operation (included in the PLATON program) was performed with the raw data set and the structure was refined from the data obtained upon SQUEEZE operation. Despite of several attempts, in case of complex (4), an accurate position of the hydrogen atoms for the lattice water molecules was not achieved. Therefore no hydrogen was added on those oxygen atoms.

All calculations and molecular graphics were preformed using either SHELXTL 2014 or Olex2 programs. Crystal data and structure refinement parameters are listed in Table 1. CCDC 1825643 (complex 1), CCDC 1825644 (complex 2), CCDC 1825646 (complex 3), CCDC 1825647 (complex 4) and CCDC 1825645 (complex 5) contain the supplementary crystallographic data. These data can be obtained from The Cambridge Crystallographic Data Center via www.cedc.cam.ac.uk/data_request.cif.

TABLE 1

Crystal data and structure refinement parameters for complexes (1), (2), (3), (4) and (5)

| Formula | (1) C$_{78}$H$_{64}$Ag$_2$N$_4$Cl$_2$P$_4$ | (2) C$_{60}$H$_{49}$Ag$_2$N$_4$Cl$_2$P$_3$ | (3) C$_{78}$H$_{64}$Ag$_2$N$_6$O$_4$P$_4$ | (4))•4H$_2$O C$_{60}$H$_{57}$Ag$_2$N$_6$O$_8$P$_3$ | (5) C$_{30}$H$_{52}$Ag$_2$N$_{16}$Cl$_2$P$_4$ |
|---|---|---|---|---|---|
| $D_{calc.}$/g cm$^{−3}$ | 1.434 | 1.335 | 1.443 | 1.374 | 1.722 |
| μ/mm$^{−1}$ | 0.80 | 0.86 | 0.72 | 0.76 | 1.31 |
| Formula Weight | 1467.85 | 1205.58 | 1488.97 | 1298.70 | 1047.39 |
| Color | Colorless | Colorless | Colorless | Colorless | Colorless |
| Shape | Block | Block | Block | Block | Block |
| T/K | 298(2) | 298(2) | 298(2) | 298(2) | 298(2) |

TABLE 1-continued

Crystal data and structure refinement parameters for complexes (1), (2), (3), (4) and (5)

| Formula | (1)<br>$C_{78}H_{64}Ag_2N_4Cl_2P_4$ | (2)<br>$C_{60}H_{49}Ag_2N_4Cl_2P_3$ | (3)<br>$C_{78}H_{64}Ag_2N_6O_4P_4$ | (4))·4H$_2$O<br>$C_{60}H_{57}Ag_2N_6O_8P_3$ | (5)<br>$C_{30}H_{52}Ag_2N_{16}Cl_2P_4$ |
|---|---|---|---|---|---|
| Crystal System | Triclinic | Triclinic | Triclinic | Triclinic | Monoclinic |
| Space Group | P-1 | P-1 | P-1 | P-1 | C2/c |
| a/Å | 12.3970(7) | 11.9900(6) | 12.4684(8) | 12.0477(6) | 22.3522(18) |
| b/Å | 12.6513(7) | 13.4064(7) | 12.7646(9) | 13.9336(6) | 7.6984(6) |
| c/Å | 13.4150(7) | 20.5531(11) | 13.4383(10) | 20.1754(10) | 25.899(2) |
| α/° | 97.372(2) | 93.164(2) | 98.117(2) | 81.223(1) | 90 |
| β/° | 116.099(1) | 93.563(2) | 116.230(2) | 84.884(1) | 114.962(1) |
| γ/° | 108.552(2) | 114.083(1) | 108.435(2) | 68.853(1) | 90 |
| V/Å$^3$ | 1700.01(16) | 2998.6(3) | 1714.0(2) | 3119.5(3) | 4040.2(6) |
| Z | 1 | 2 | 1 | 2 | 4 |
| Wavelength/Å | 0.71073 | 0.71073 | 0.71073 | 0.71073 | 0.71073 |
| Radiation type | Mo-Kα | Mo-Kα | Mo-Kα | Mo-Kα | Mo-Kα |
| 2θ$_{min}$/° | 6.00 | 6.00 | 5.80 | 5.80 | 6.20 |
| 2θ$_{max}$/° | 56.60 | 52.80 | 53.00 | 52.60 | 52.80 |
| Measured Refl. | 28423 | 55827 | 31251 | 57586 | 38314 |
| Independent Refl. | 8045 | 12266 | 7051 | 12623 | 4113 |
| Reflections Used | 6244 | 8456 | 5461 | 10176 | 3876 |
| R$_{int}$ | 0.032 | 0.043 | 0.051 | 0.024 | 0.019 |
| Parameters | 406 | 622 | 424 | 712 | 244 |
| $^a$GooF | 1.050 | 1.040 | 1.070 | 1.040 | 1.190 |
| $^c$wR$_2$ | 0.083 | 0.107 | 0.154 | 0.129 | 0.073 |
| $^b$R$_1$ | 0.037 | 0.045 | 0.058 | 0.039 | 0.029 |

$^a$GOF = $[\Sigma[w(F_o^2 - F_c^2)^2]/(N_o - N_v)]^{1/2}$ (N$_o$ = number of observations, N$_v$ = number of variables).
$^b$R$_1$ = $\Sigma||F_o| - |F_c||/\Sigma|F_o|$.
$^c$wR$_2$ = $[(\Sigma w(F_o^2 - F_c^2)^2/\Sigma|F_o|^2)]^{1/2}$

Example 9—X-Ray Crystallographic Analyses

Single crystal X-ray crystallographic analyses revealed the molecular structures for all complexes (1) to (5). Among them the perspective view for the structures (1), (2), (3), (4) and (5) are depicted in FIGS. 4, 5, 6, 7, and 8 and selected metric parameters are listed in Tables 2, 3, 4, and 5. In case of complexes (1), (3) and (5) only one half of the formula is present in the asymmetric unit, with other half consisting of symmetry equivalent atoms.

The X-ray structures of complexes (1), (3) and (5) (FIGS. 4, 6 and 8, respectively) revealed that in all three cases the two Ag(I) centers were equivalent and each metal center resided in a distorted tetrahedral coordination environment. To assess the distortion from the ideal tetrahedral geometry around the Ag centers, a simple index (τ4) developed by Houser and co-workers was calculated for complexes (1) and (5). This simple index is unity for a perfect tetrahedron and zero for square planar geometry. The τ4 values for complexes (1) and (5) were 0.89 and 0.78 respectively suggesting the coordination environment around the Ag centers was distorted tetrahedral in these complexes. Two μ-pyrazolates bridged the Ag(I) centers and the other two coordination sites of each Ag(I) center were occupied by two PPh$_3$ ligands. The two Ag atoms along with four N atoms (Ag1, Ag1a, N1, N2, N1a, N2a) of the bridging pyrazolates formed a centrosymmetric six-membered ring in a chair conformation, with one Ag-atom on either side of the planes defined by the pyrazolate rings and at a Ag . . . Ag distance of 4.209(4) Å(1) and 4.205(3) Å(5). This twisted metallacyclic conformation is rare in literature, but not unprecedented. Although complexes (1) and (5) are structurally similar, careful scrutiny of the metric parameters revealed certain differences (Table 1): The average Ag—N bond length in complex (1), 2.319(2) Å, was shorter than that in complex (5) (2.367(3) A); The P—Ag—P angle in complex (1), 118.82(2°), was noticeably more acute than the corresponding 140.43(3°) angle in complex (5) and the same applied to the N—Ag—N bond angles, 98.00(7°) in complex (1) and 103.37(9°) in complex (5), the differences attributed to the steric bulk of PTA compared to PPh$_3$. Consequently, the average N1-Ag1-P1 angle in complex 1 (109.32(6)°) was more obtuse than in complex 5 (101.80(7)°). The average Ag1-P1 bond lengths for these two complexes, 2.4921(7) A complex (1) and 2.4972(8) A complex (5), respectively, were indistinguishable.

TABLE 2

Selected bond distances (Å) and angles (°) for complexes (1) and (5).

| | Complex (1) | Complex (5) |
|---|---|---|
| Ag1-P1 | 2.5003(7) | 2.5345(8) |
| Ag1-P2 | 2.4838(7) | 2.4598(7) |
| Ag1-N1 | 2.285(2) | 2.336(2) |
| Ag1-N2a | 2.353(2) | 2.398(3) |
| P2-Ag1-P1 | 118.82(2) | 140.43(3) |
| N1-Ag1-P2 | 110.20(6) | 109.52(7) |
| N1-Ag1-P1 | 115.09(6) | 100.00(7) |
| N1-Ag1-N2a | 98.00(7) | 103.37(9) |
| N2a-Ag1-P2 | 105.32(6) | 105.46(7) |
| N2-Ag1-P1 | 106.68(6) | 92.23(7) |

The a-labeled atoms were generated by the -x + 1, -y, -z + 1 symmetry operation

Figure 4:
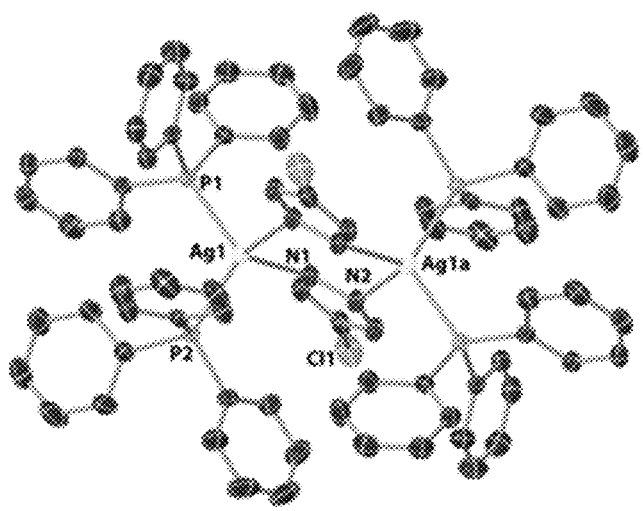
FIG. 4 shows a perspective view of the molecular structure of complex (1) where the symmetry equivalent atoms are generated by −x+1, −y, −z+1.
Figure 5:
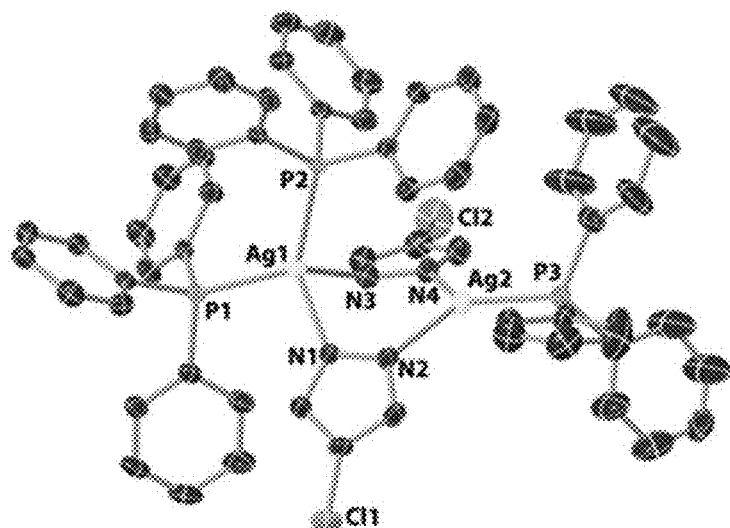
FIG. 5 shows a perspective view of the molecular structure of complex (2), where the symmetry equivalent atoms are generated by −x+1, −y+2, −z+1.
Figure 6:
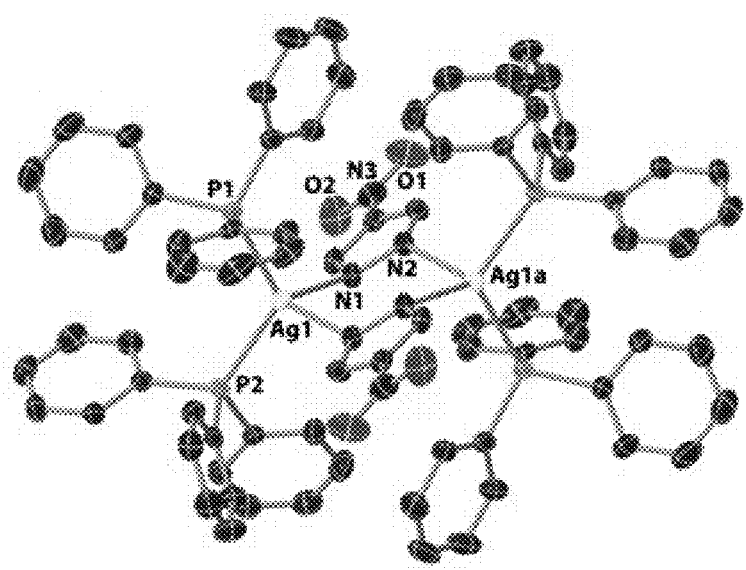
FIG. 6 shows a perspective view of the molecular structure of complex (3).
Figure 7:
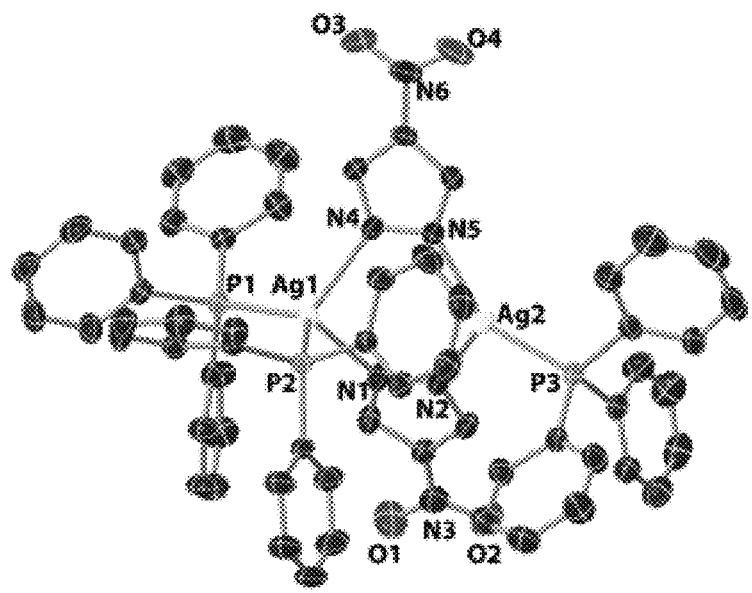
FIG. 7 shows a perspective view of the molecular structure of complex (4).
Figure 8:
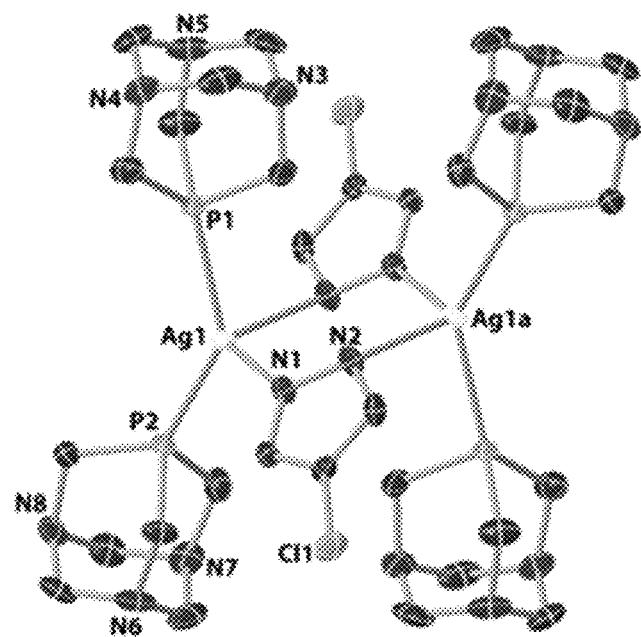
FIG. 8 shows a perspective view of the molecular structure of complex (5), where the symmetry equivalent atoms are generated by −x+1, −y, −z+1.
Figure 9:
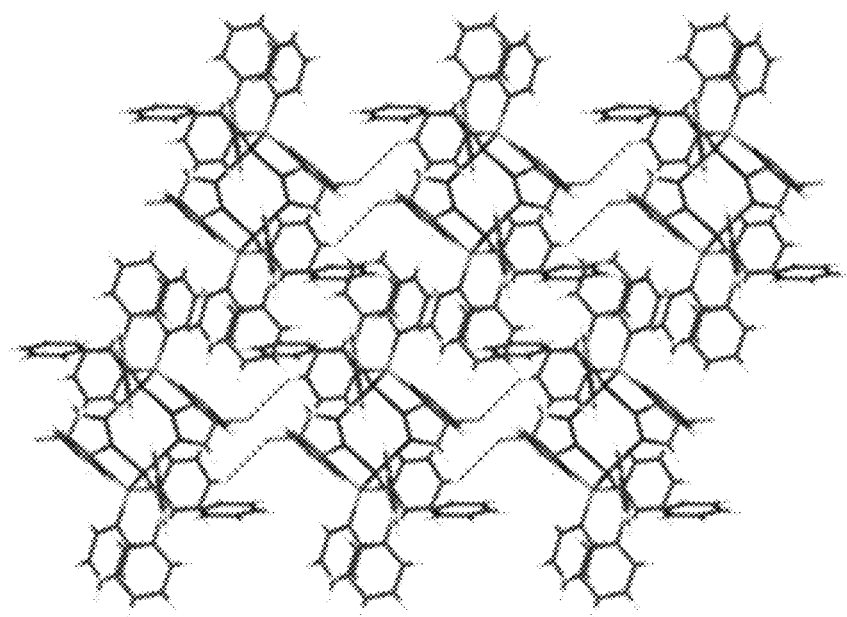
FIG. 9 shows a packing pattern of complex (1) along b axis, with the dotted lines representing weak C—H—Cl intermolecular interactions.
Figure 10:
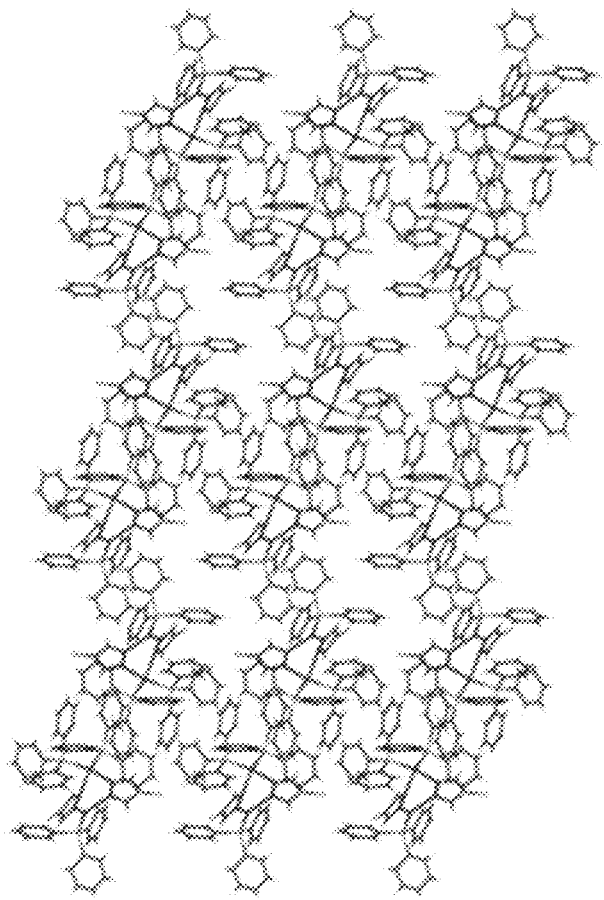
FIG. 10 shows a packing pattern of complex (2) along a axis.
Figure 11:
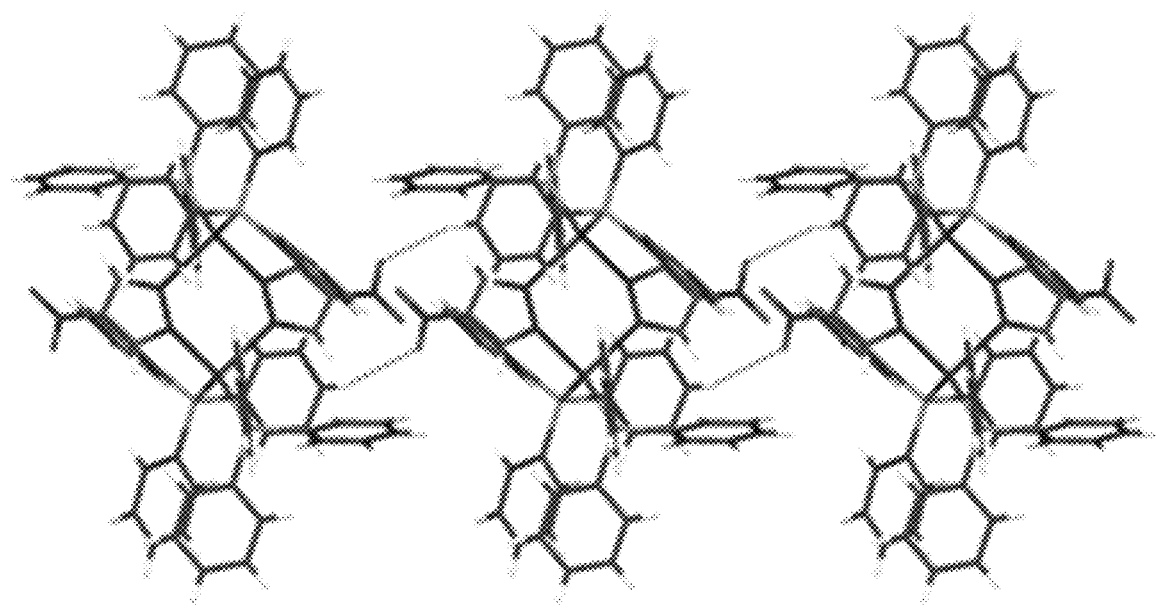
FIG. 11 shows a packing pattern of complex (3) along c axis, with the dotted lines representing weak C—H—O intermolecular interactions.
Figure 12:
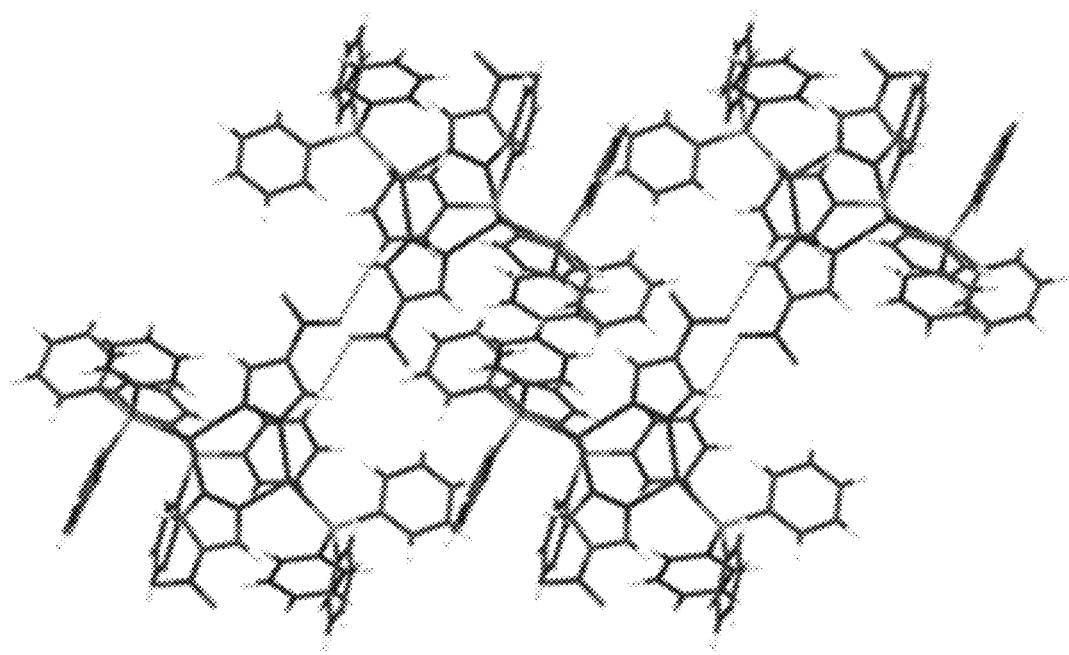
FIG. 12 shows a packing pattern of complex (4) along a axis, with the dotted lines representing weak C—H—O intermolecular interactions.
Figure 13:
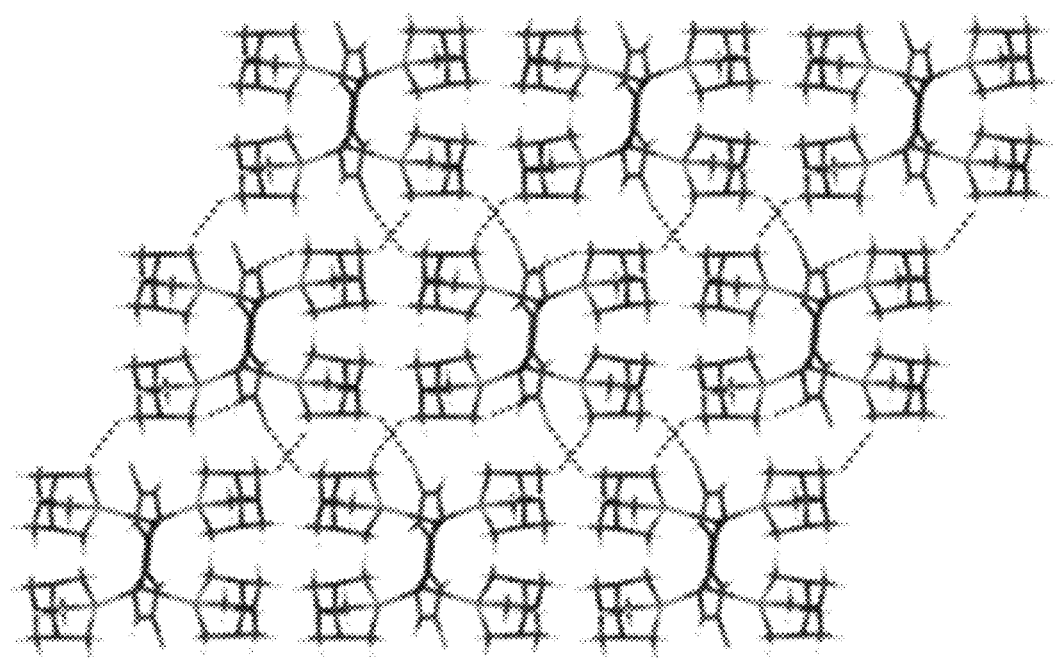
FIG. 13 shows a packing pattern of complex (5) along c axis, with the dotted lines representing weak C—H—Cl intermolecular interactions.
Figure 14:
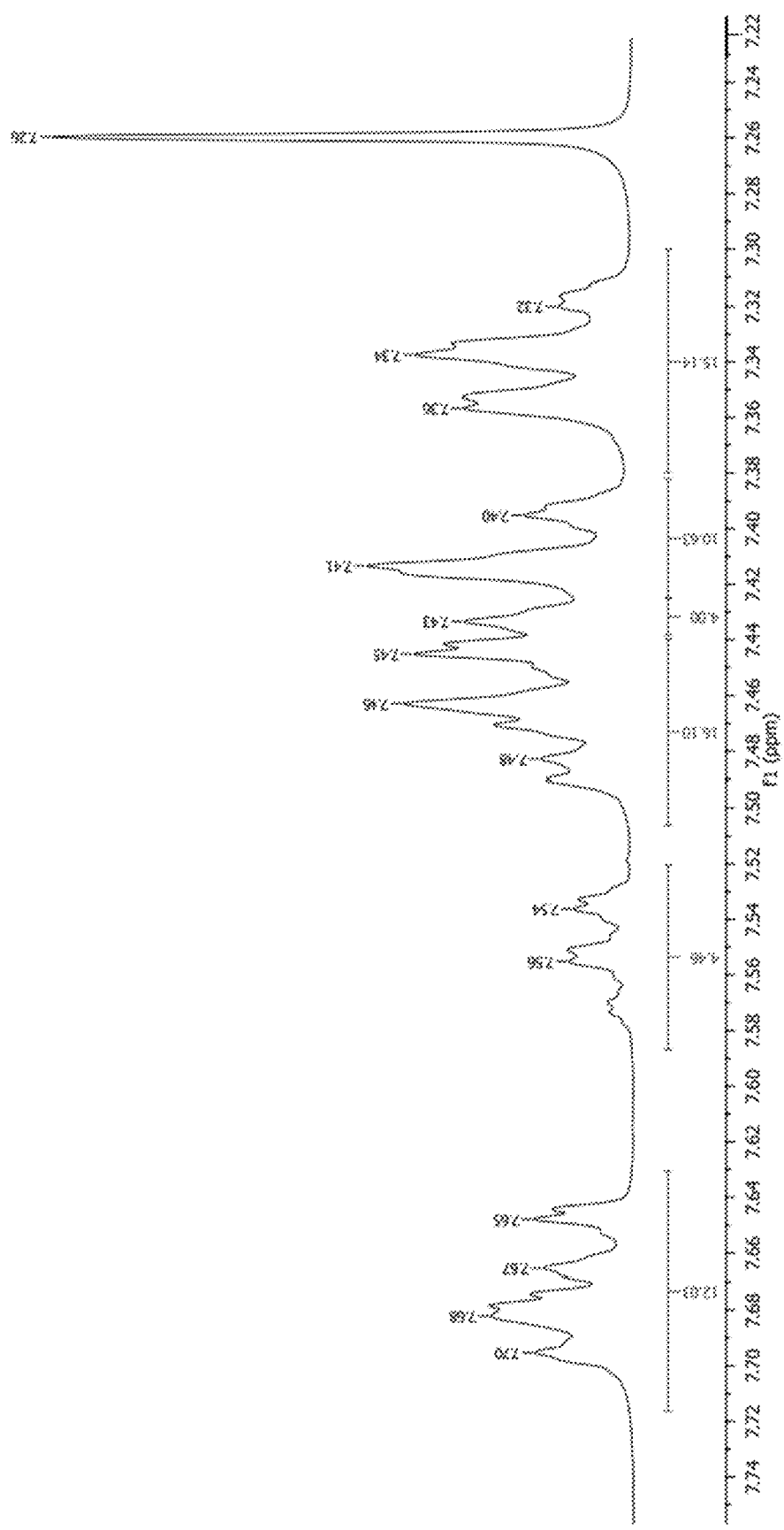
FIG. 14 shows a $^1$H NMR for complex (1).
Figure 15:
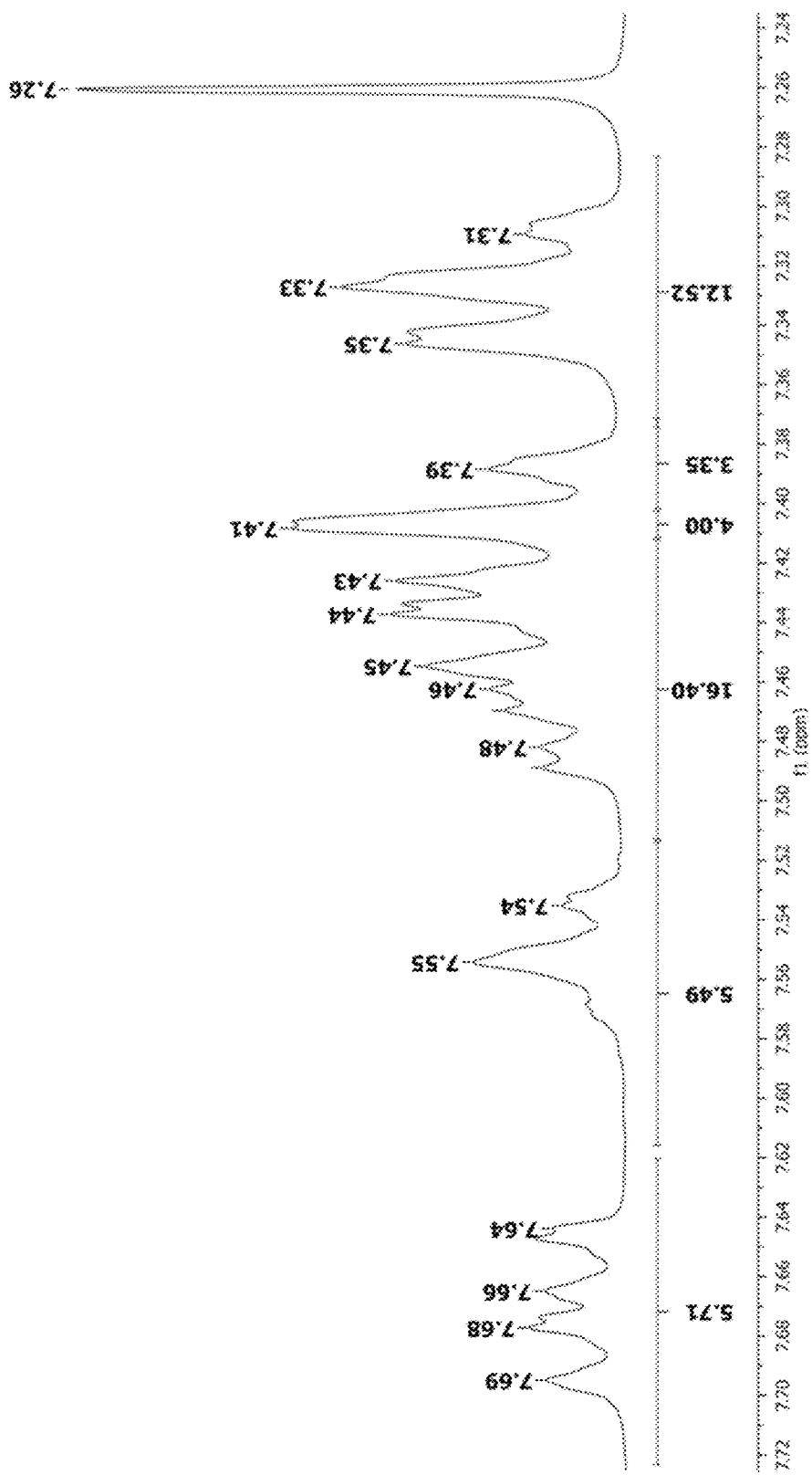
FIG. 15 shows a $^1$H NMR for complex (2).
Figure 16:
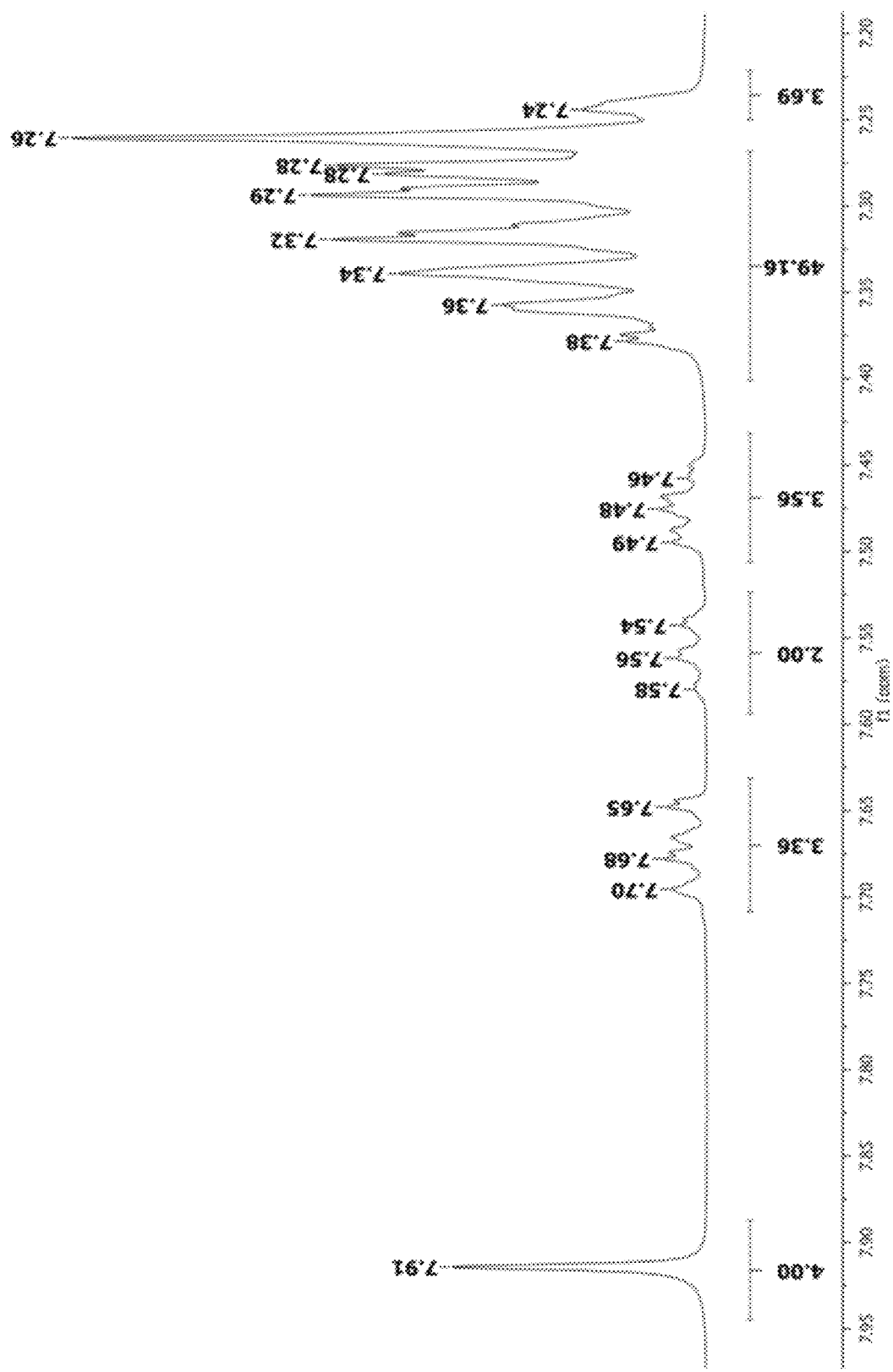
FIG. 16 shows a $^1$H NMR for complex (3).
Figure 17:
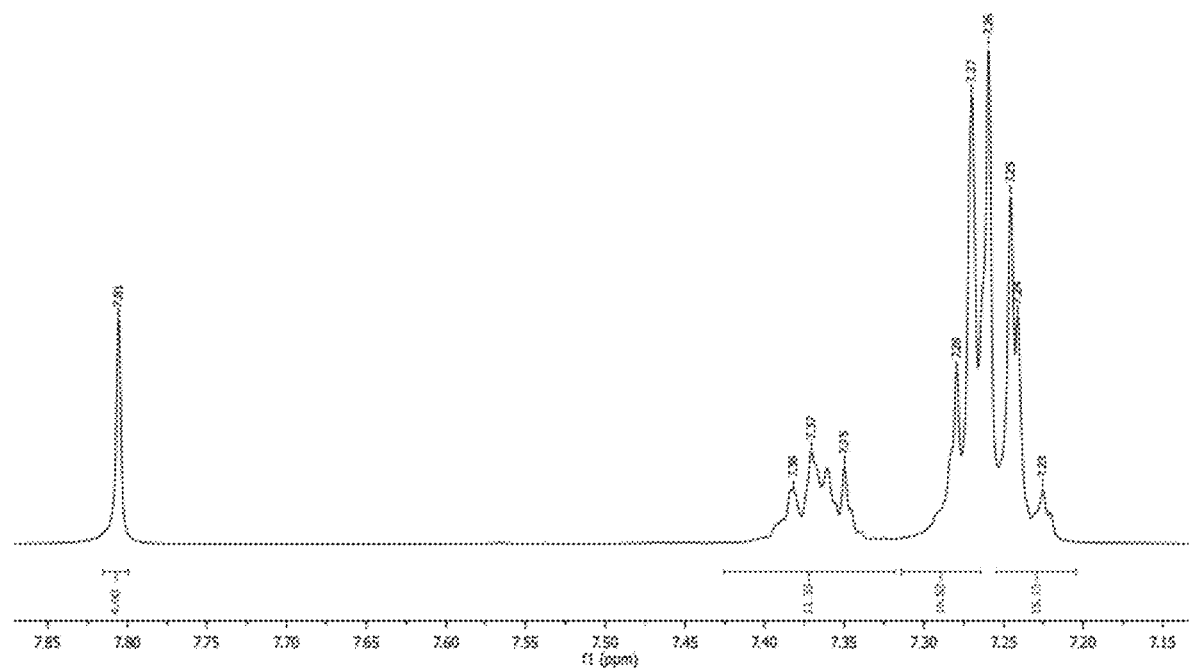
FIG. 17 shows a $^1$H NMR for complex (4).
Figure 18:
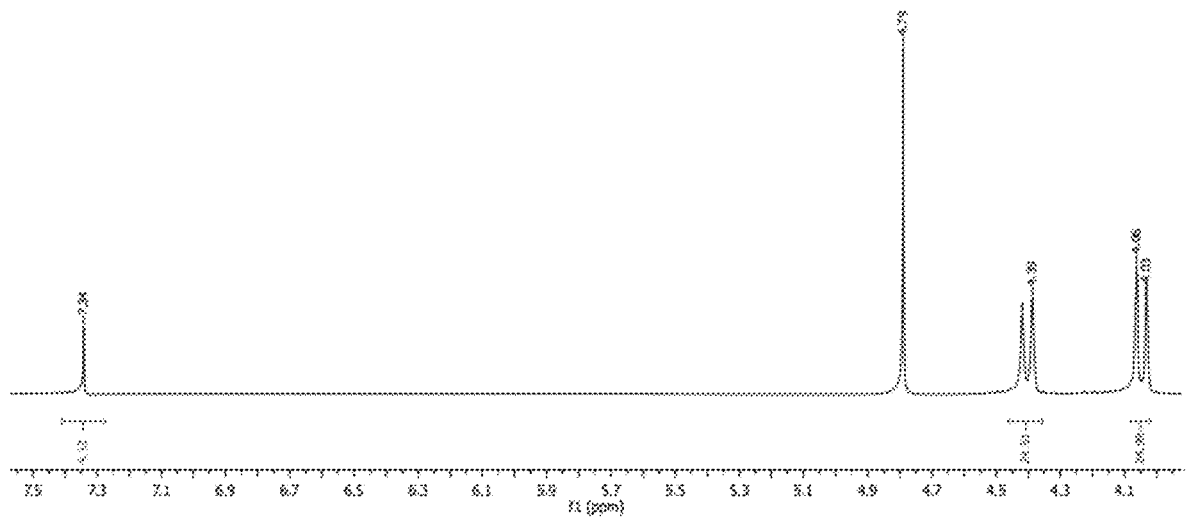
FIG. 18 shows a $^1$H NMR for complex (5).
Figure 19:
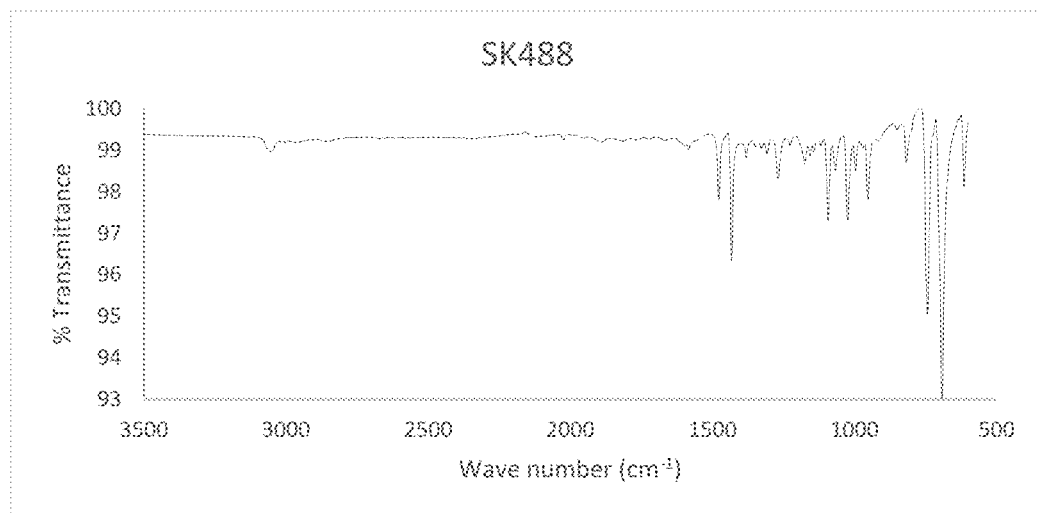
FIG. 19 shows a IR spectrum for complex (1).
Figure 20:
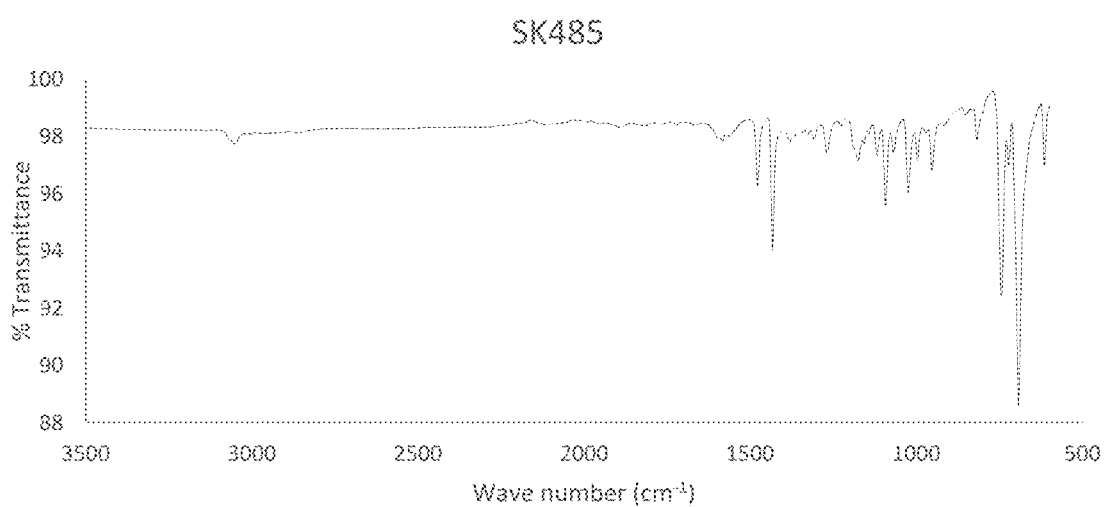
FIG. 20 shows a IR spectrum for complex (2).
Figure 21:
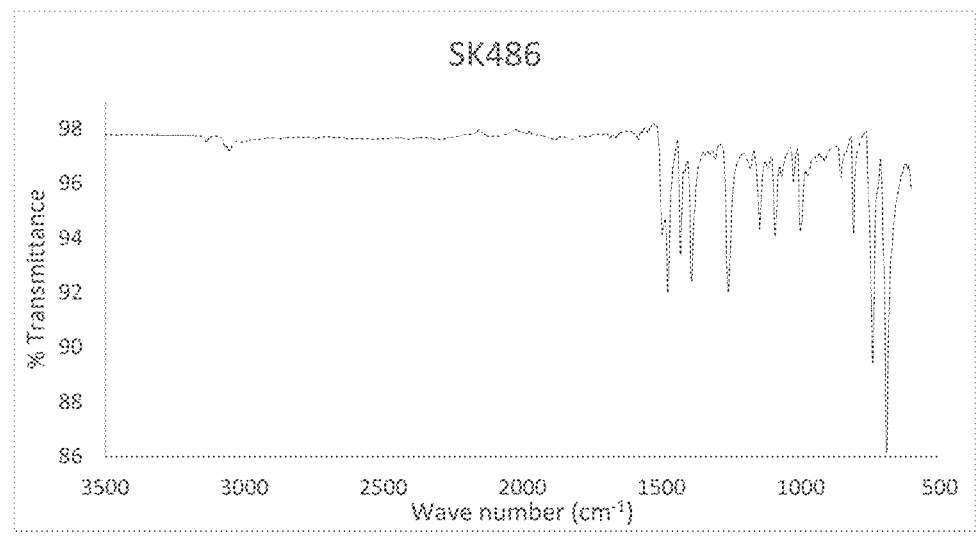
FIG. 21 shows a IR spectrum for complex (3).
Figure 22:
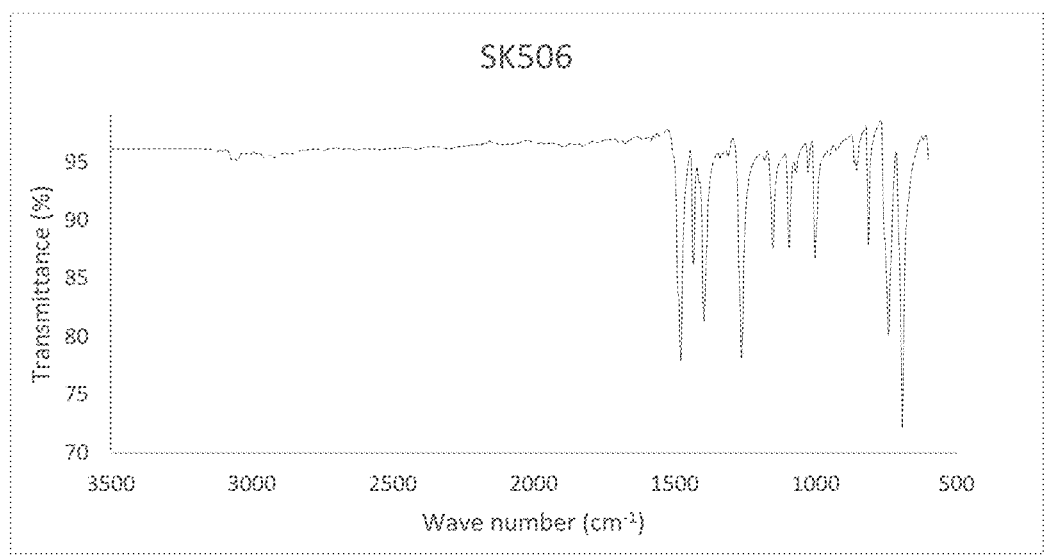
FIG. 22 shows a IR spectrum for complex (4).
Figure 25:
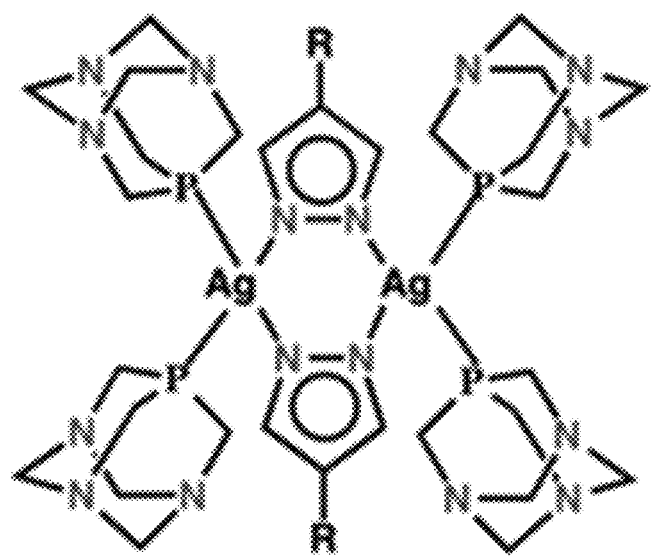
FIG. 25 shows a bis(3,4,5-R-pyrazolido)tetrakis(1,3,5-triazaphosphaadamantane)disilver(I) complex (6) wherein $R^3$ and $R^5$ are hydrogen and $R^4$=R can be H. Cl, or $NO_2$.
Figure 26:
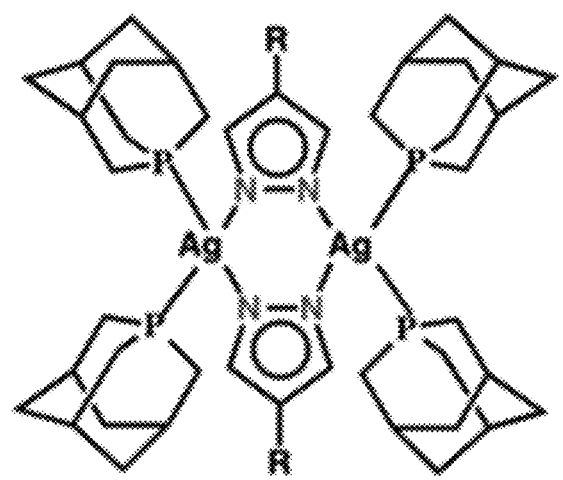
FIG. 26 shows bis(3,4,5-R-pyrazolido)tetrakis(phosphaadamantane)disilver(I) complex (7) wherein $R^3$ and $R^5$ are hydrogen and $R^4$R can be H. Cl, or $NO_2$.
Figure 27:
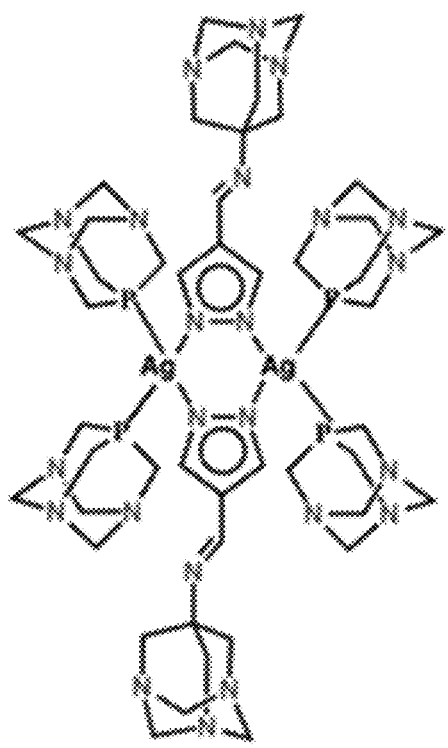
FIG. 27 shows a bis(μ-4-1,3,5-triazaadamantane-imine-pyrazolido)tetrakis(1,3,5-triazaphosphaadamantane)disilver (I) complex (8).
Figure 28:
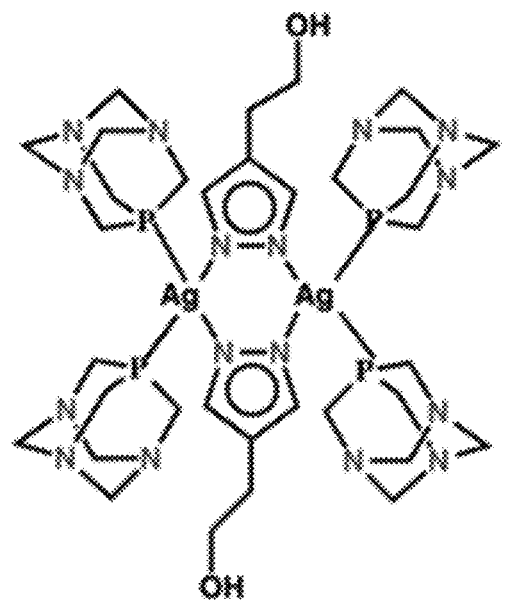
FIG. 28 shows a bis(μ-4-hydroxyethyl-pyrazolido)tetrakis (1,3,5-triazaphospha-adamantane)disilver(I) complex (9).
Figure 29:
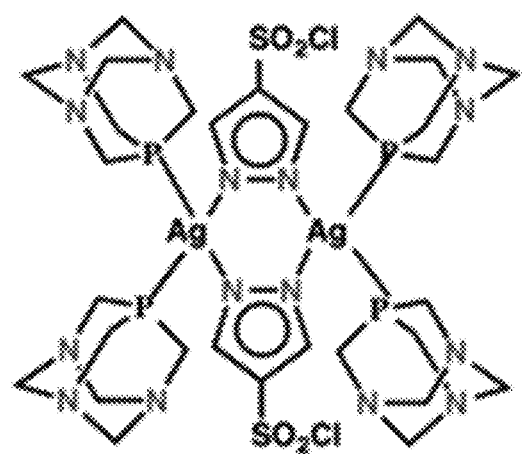
FIG. 29 shows a bis(μ-4-sulfonylchloride-pyrazolido)tetrakis(1,3,5-triazaphospha-adamantane)disilver(I) complex (10).
Figure 30:
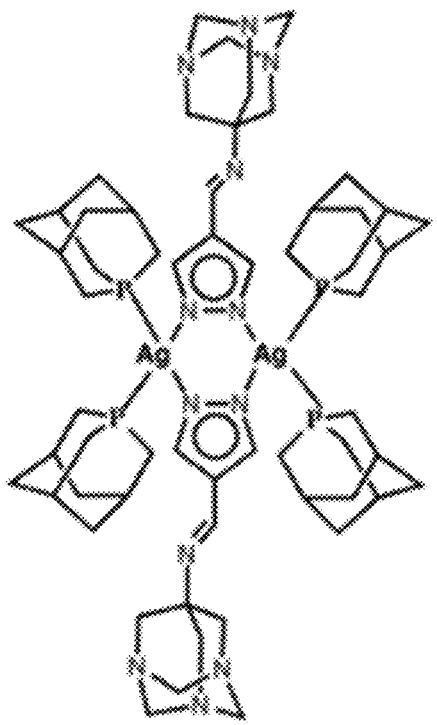
FIG. 30 shows a bis(μ-4-1,3,5-triazaadamantane-imine-pyrazolido)tetrakis(phospha-adamantane)disilver(I) complex (11).
Figure 31:
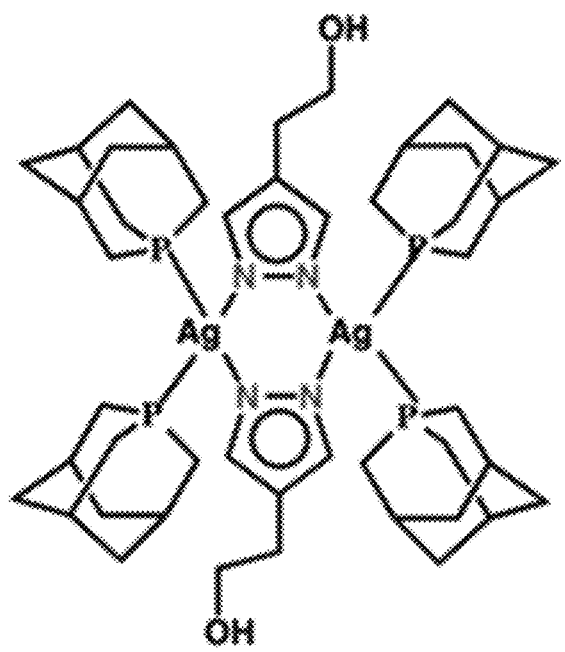
FIG. 31 shows a bis(μ-4-hydroxyethyl-pyrazolido)tetrakis (phosphaadamantane)disilver(I) complex (12).
Figure 32:
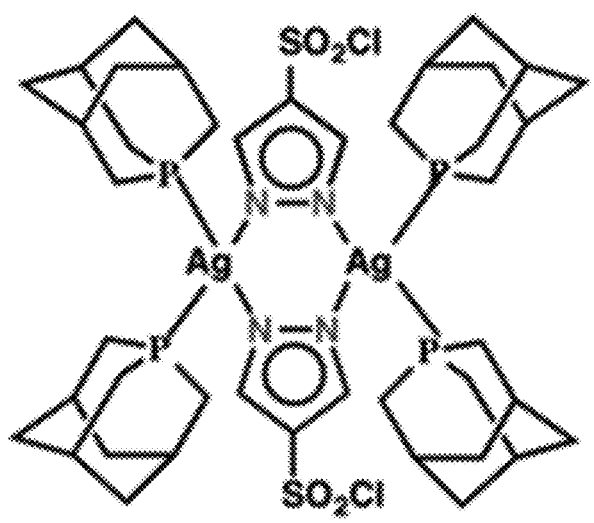
FIG. 32 shows a bis(μ-4-sulfonylchloride-pyrazolido)tetrakis (phosphandamantane)disilver(I) complex (13).
Figure 33:
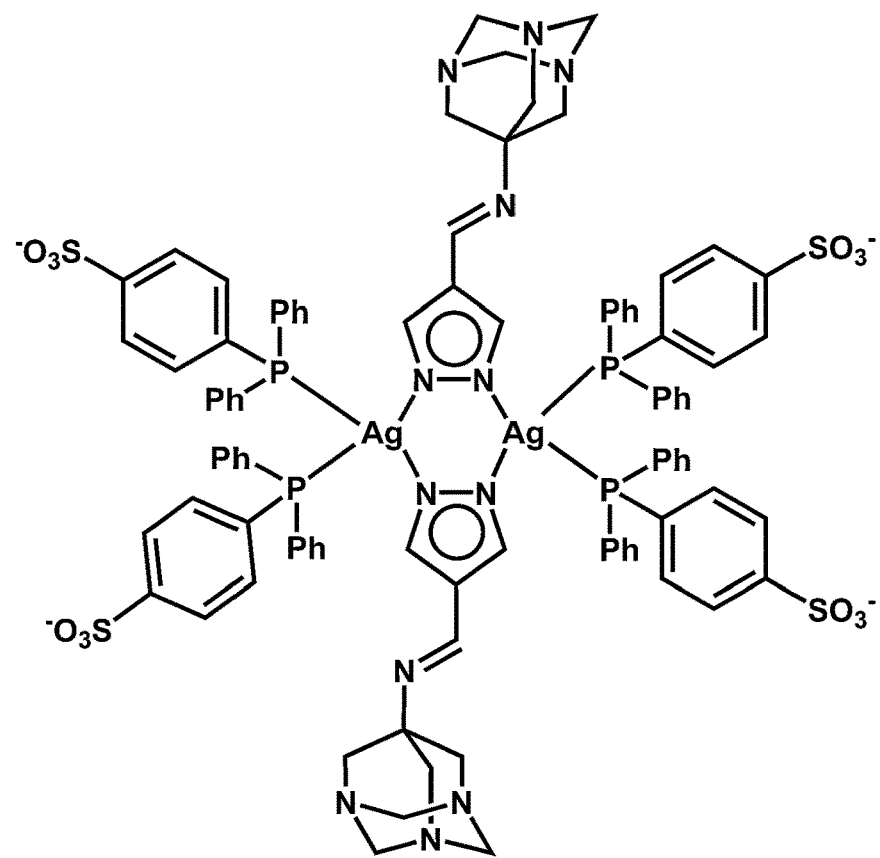
FIG. 33 shows a bis(μ-4-1,3,5-triazaadamantane-imine-pyrazolido)tetrakis((4-sulfophenyl)diphenylphosphine)disilver(I) complex (14).
Figure 34:
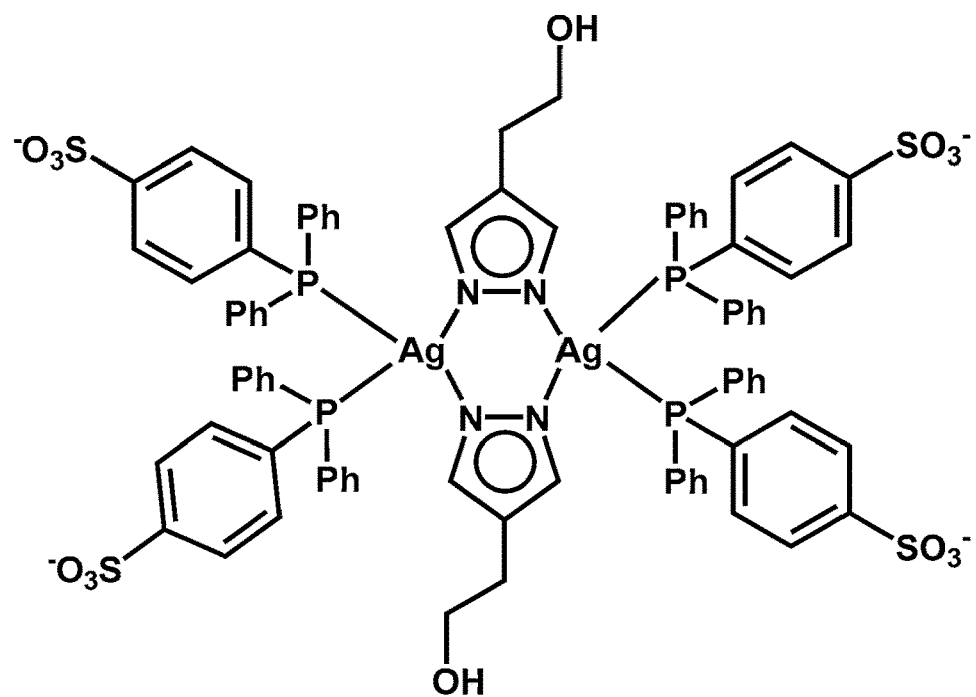
FIG. 34 shows a bis(μ-4-hydroxyethyl-pyrazolido)tetrakis ((4-sulfophenyl)diphenylphosphine)disilver(I) complex (15).
Figure 35:
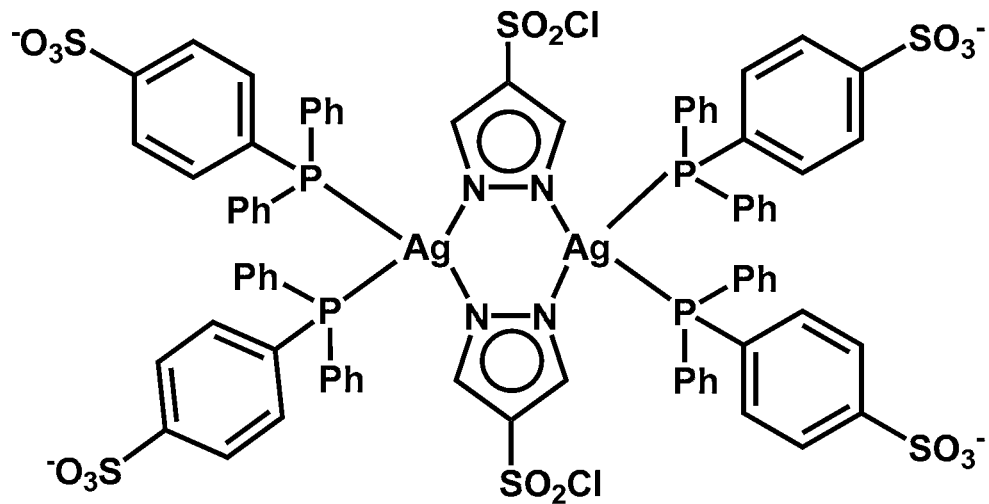
FIG. 35 shows a bis(μ-4-sulfonylchloride-pyrazolido)tetrakis((4-sulfophenyl)diphenylphosphine)disilver(I) complex (16).
Figure 36:
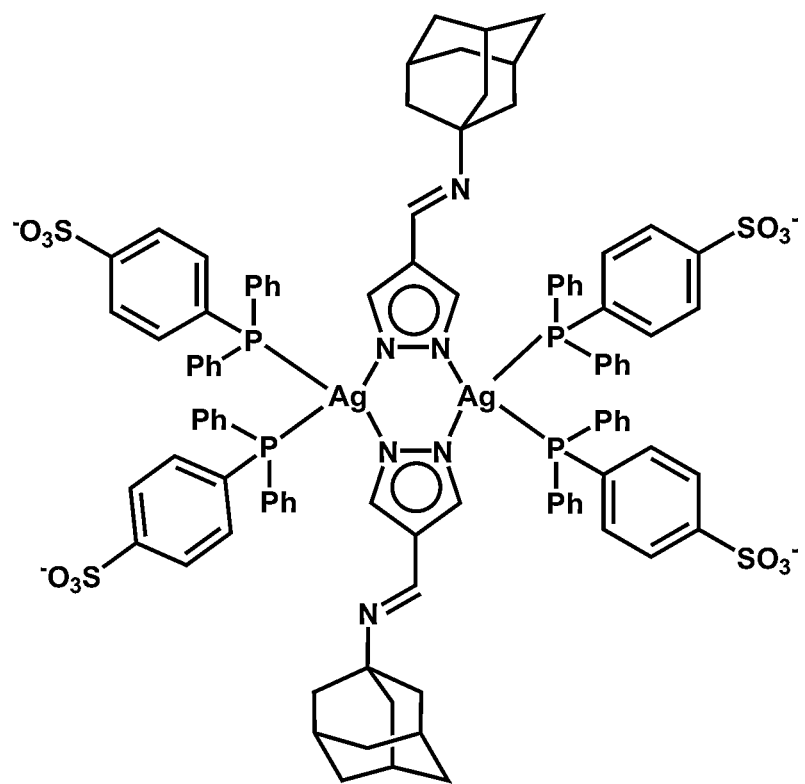
FIG. 36 shows a bis(μ-4-adamantane-imine-pyrazolido) tetrakis((4-sulfophenyl)diphenylphosphine)disilver(I) complex (17).
Figure 37:
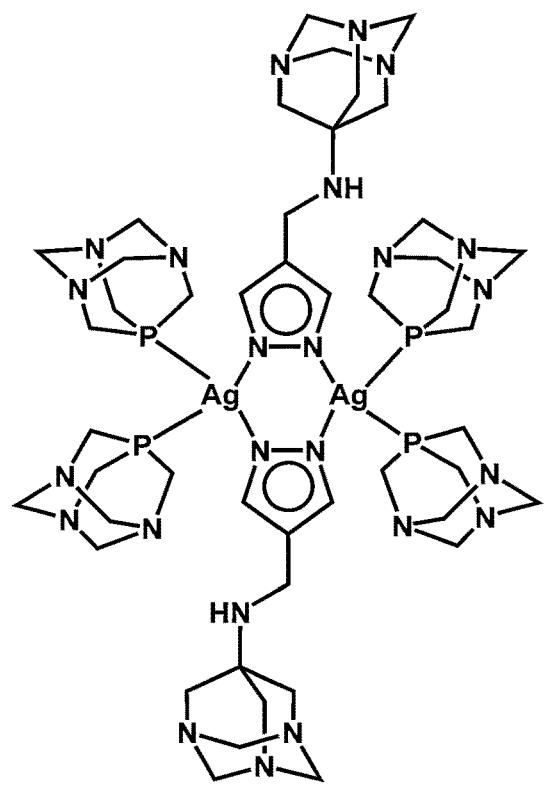
FIG. 37 shows a bis(μ-4-1,3,5-triazaadamantane-amine-pyrazolido)tetrakis(1,3,5-triazaphosphaadamantane)disilver (I) complex (18).
Figure 38:
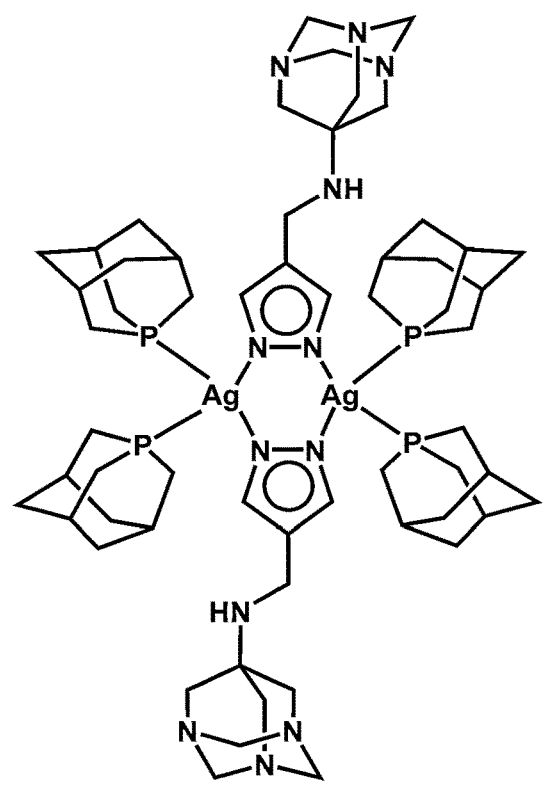
FIG. 38 shows a bis(μ-4-1,3,5-triazaadamantane-amine-pyrazolido)tetrakis(phosphaadamantane)disilver(I) complex (19).
Figure 39:
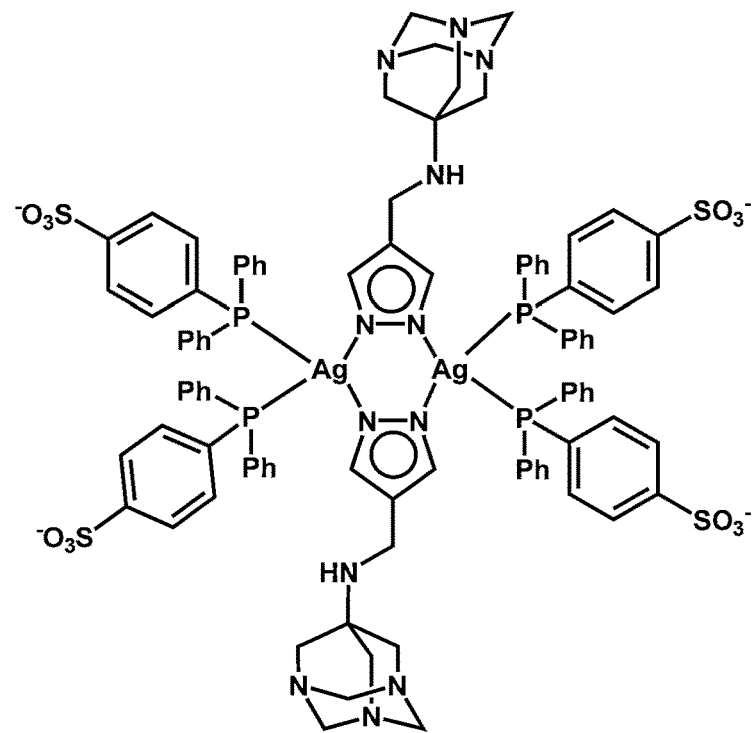
FIG. 39 shows a bis(μ-4-1,3,5-triazaadamantane-amine-pyrazolido)tetrakis((4-sulfophenyl)-diphenylphosphine)disilver(I) complex (20).
Figure 40:
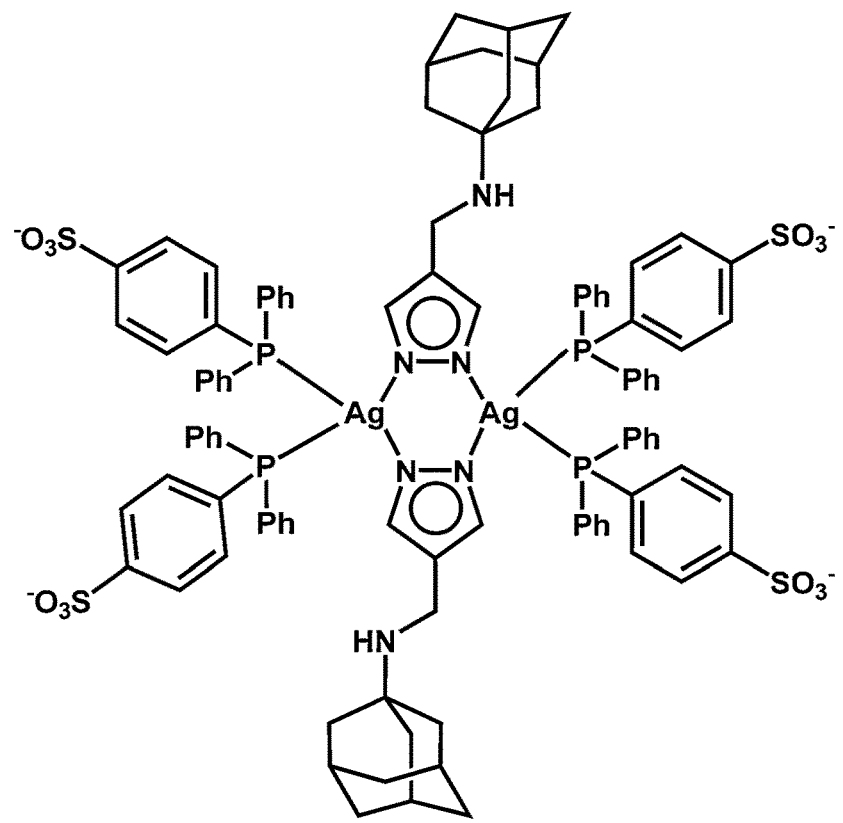
FIG. 40 shows a bis(μ-4-adamantane-amine-pyrazolido) tetrakis((4-sulfophenyl) diphenylphosphine)disilver(I) complex (21).
Figure 41:
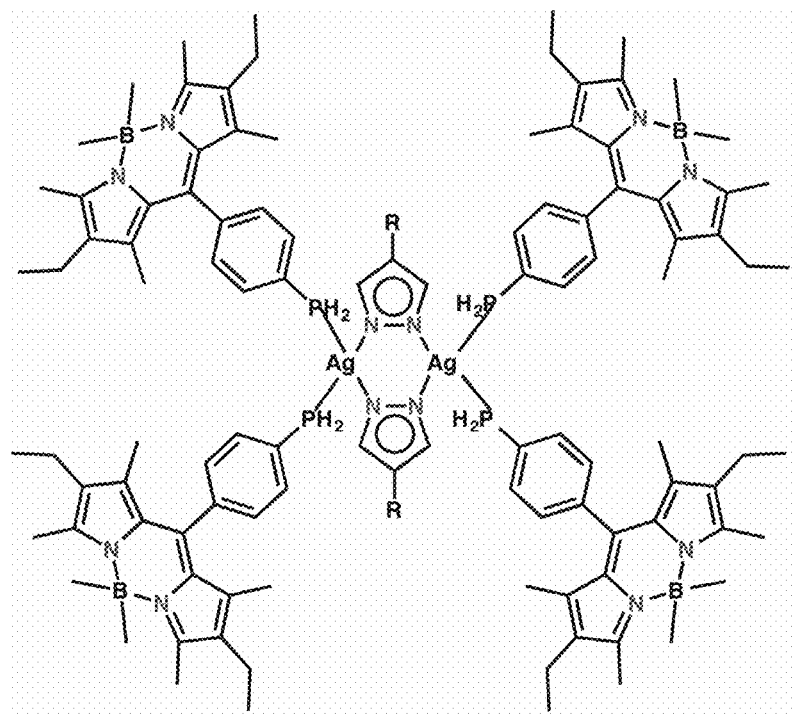
FIG. 41 shows a bis(3,4-R-pyrazolido)tetrakis(8-((4-phosphino)phenyl)-4,4-dimethyl-1,3,5,7-tetramethyl2,6-diethyl-4-bora-3a,4a-diaza-s-indacene)disilver(I) complex (22) wherein $R^3$ and R are hydrogen and $R^4$=R can be H. Cl, or $NO_2$.
Figure 42:
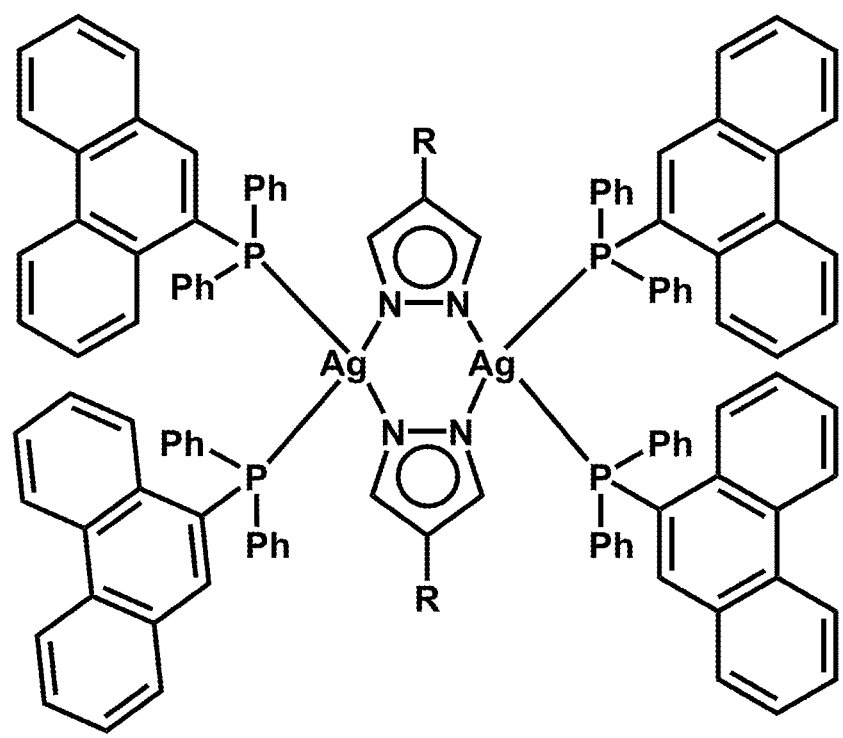
FIG. 42 shows a bis(3,4,5-R-pyrazolido)tetrakis (phenanthrene diphenylphosphine)disilver(I) complex (23) wherein $R^3$ and Rare hydrogen and R=R can be H. Cl, or $NO_2$.
Figure 43:
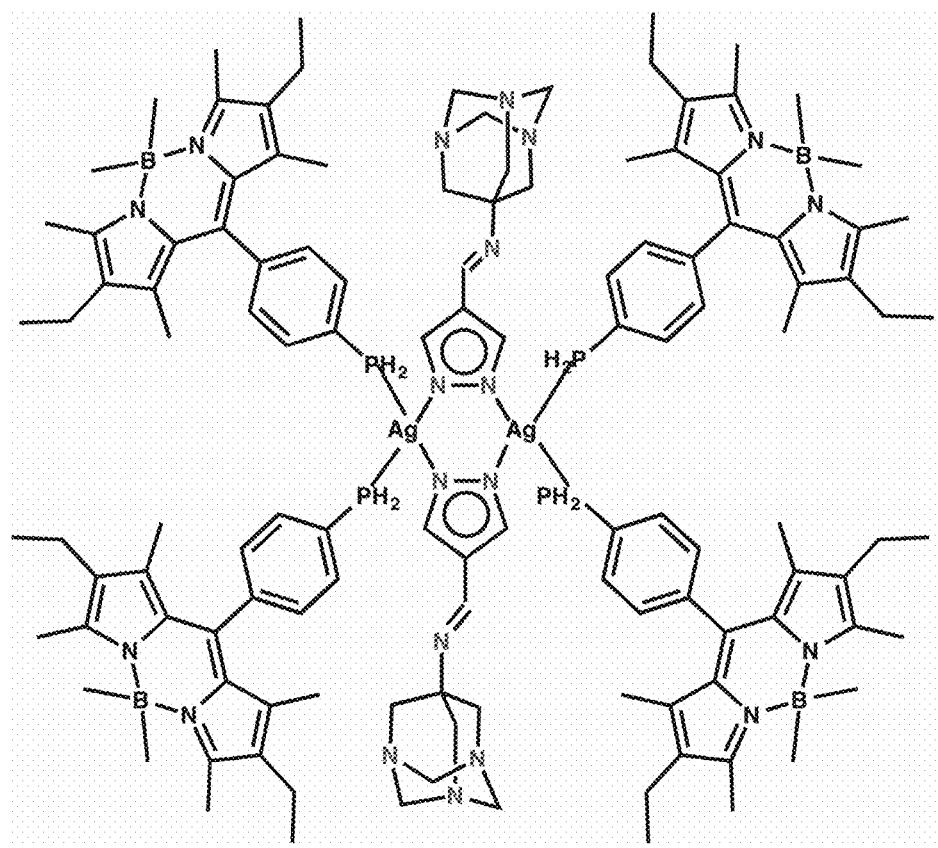
FIG. 43 shows a bis(μ-4-1,3,5-triazaadamantane-imine-pyrazolido)tetrakis(8-((4-phosphino)phenyl)-4,4-dimethyl-1,3,5,7-tetramethyl2,6-diethyl-4-bora-3a,4a-diaza-s-indacene)disilver(I) complex (24).
Figure 44:
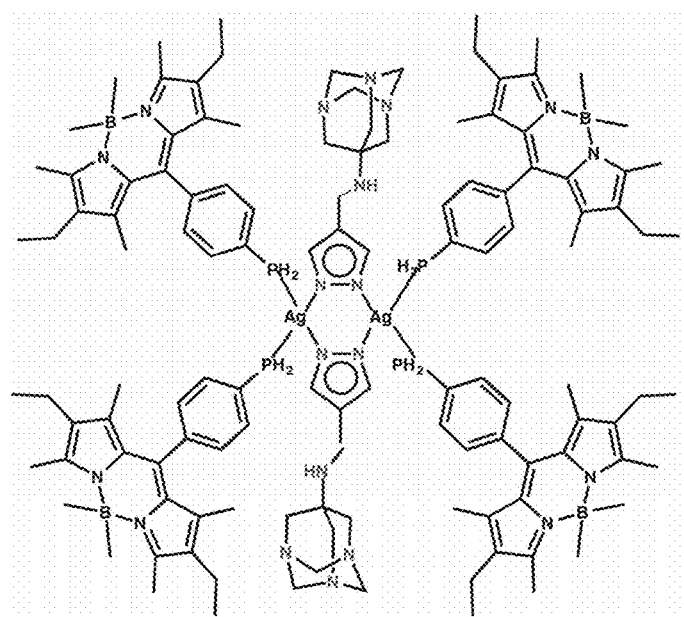
FIG. 44 shows a bis(μ-4-1,3,5-triazaadamantane-amine-pyrazolido)tetrakis((8-((4-phosphino)phenyl)-4,4-dimethyl-1,3,5,7-tetramethyl2,6-diethyl-4-bora-3a,4a-diaza-s-indacene)disilver(I) complex (25).
Figure 45:
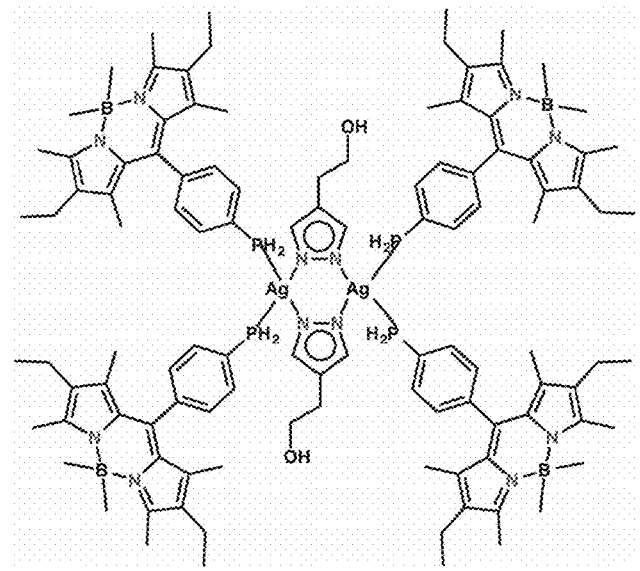
FIG. 45 shows a bis(μ-4-hydroxyethyl-pyrazolido)tetrakis ((8-((4-phosphino)phenyl)-4,4-dimethyl-1,3,5,7-tetramethyl2,6-diethyl-4-bora-3a,4a-diaza-s-indacene)disilver(I) complex (26).
Figure 46:
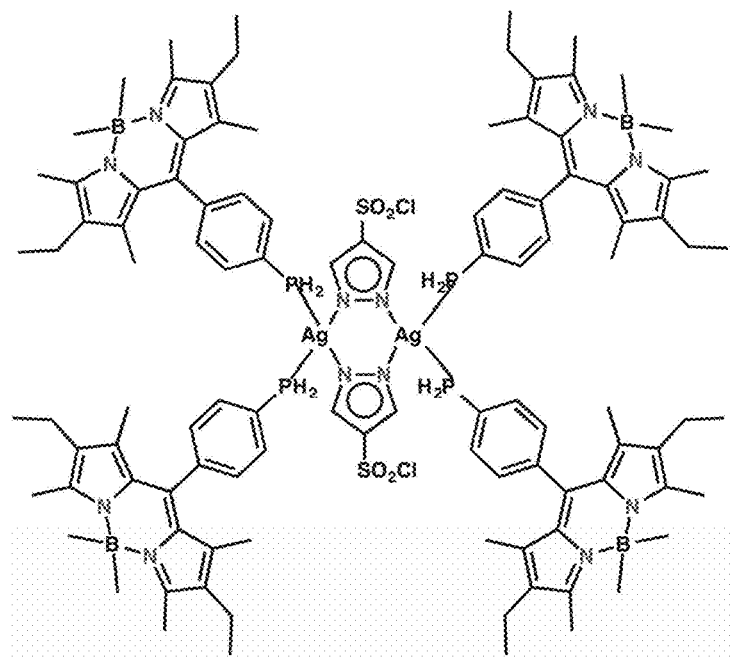
FIG. 46 shows a bis(μ-4-sulfonylchloride-pyrazolido)tetrakis((8-((4-phosphino)phenyl)-4,4-dimethyl-1,3,5,7-tetramethyl2,6-diethyl-4-bora-3a,4a-diaza-s-indacene)disilver (I) complex (27).
Figure 47:
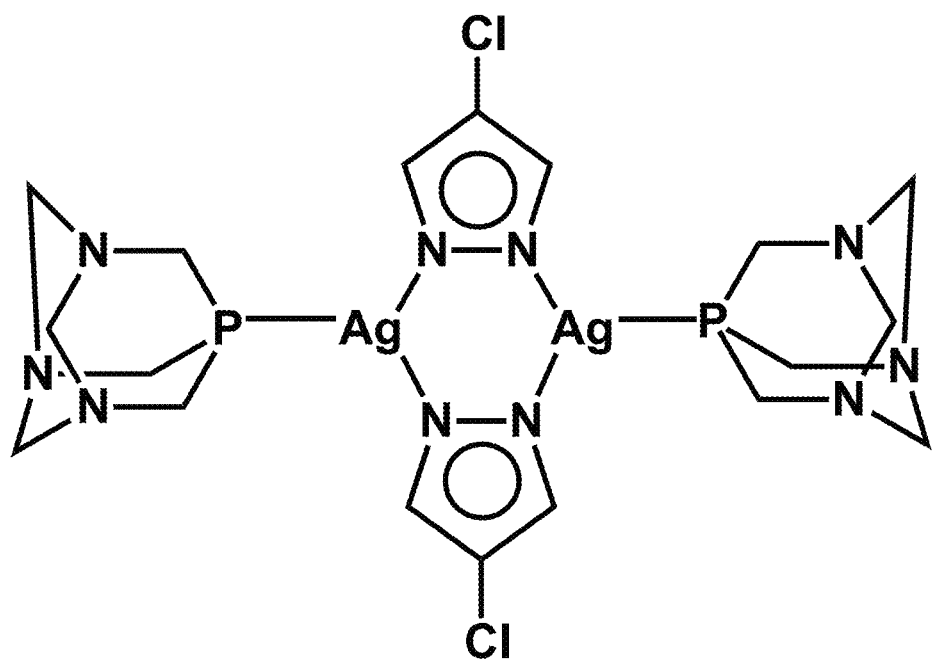
FIG. 47 shows a bis(μ-4-chloride-pyrazolido)bis(1,3,5-triazaphospbaadamantane)disilver(I) complex (28).
Figure 48:
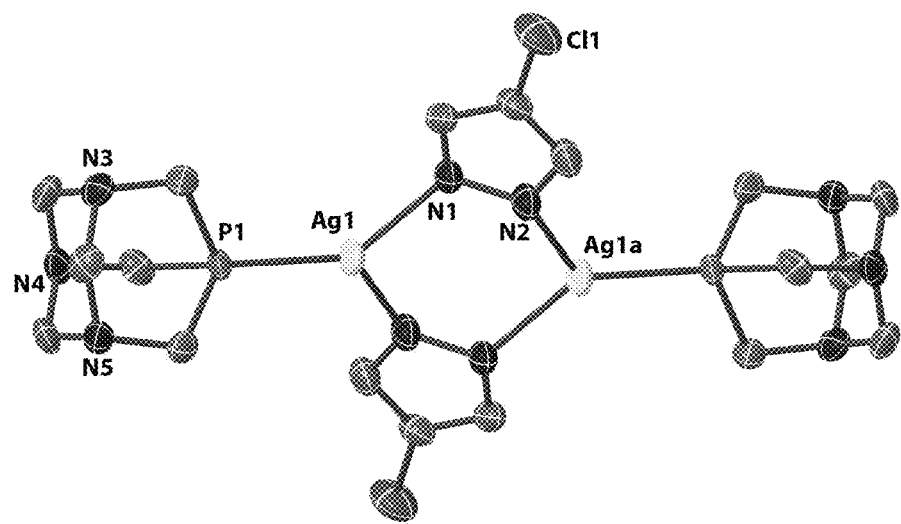
FIG. 48 shows a perspective view of the molecular structure of complex (28).
Figure 49:
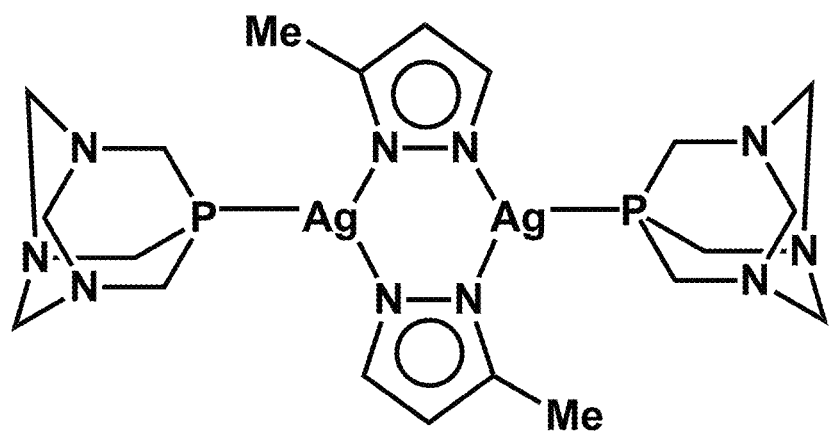
FIG. 49 shows a bis(μ-3-methyl-pymzolido)bis(1,3,5-triazaphosphaadamantane)disilver(I) complex (29).
Figure 50:
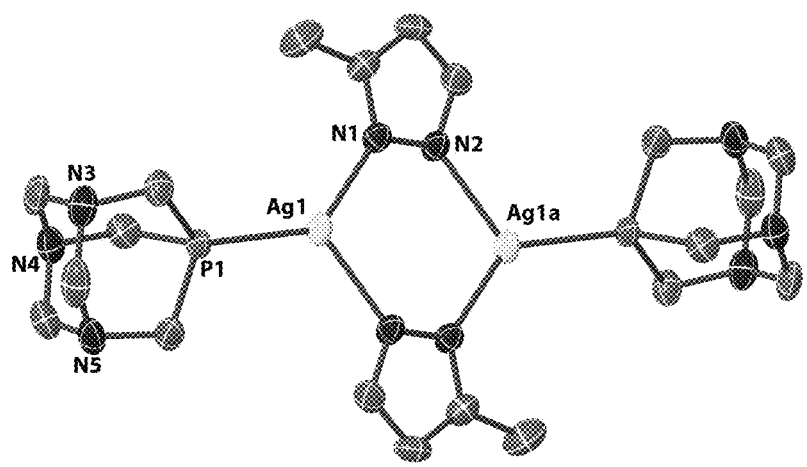
FIG. 50 shows a perspective view of the molecular structure of complex (29).
Figure 51A:
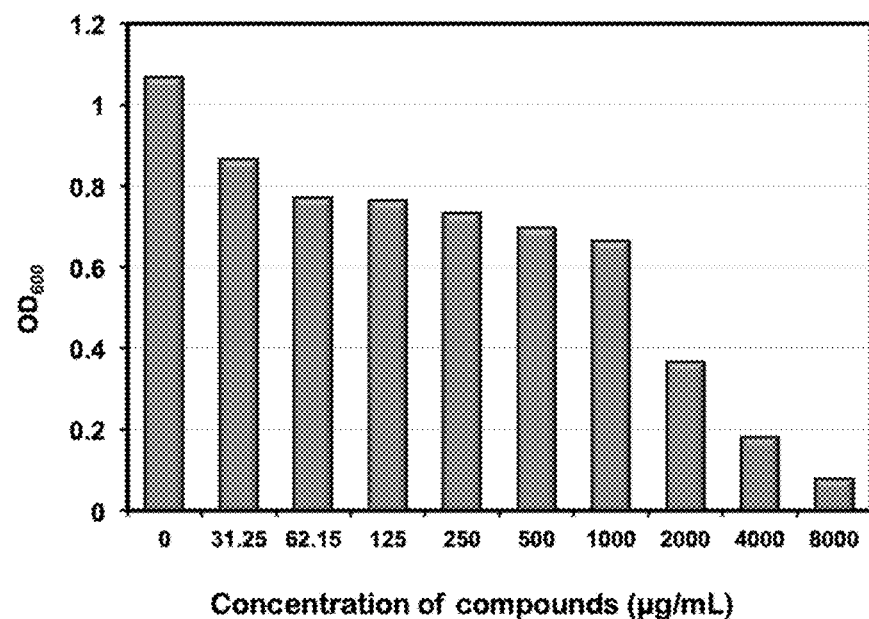
FIGS. 51A-51B show the results of bacterial eradication by compounds of complex (5) and complex (29) assessed using the optical density method.
Figure 51B:
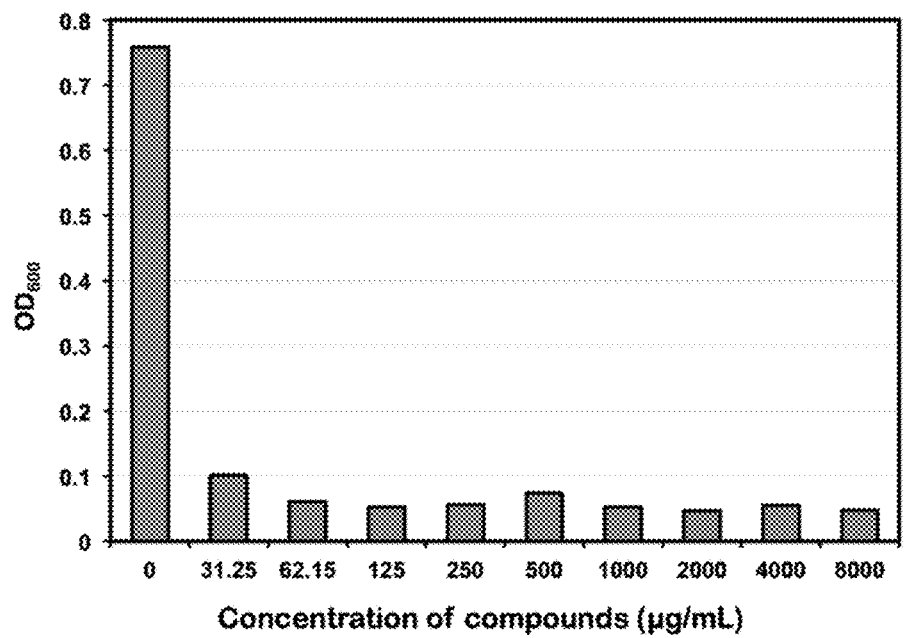

The crystal structure of complex (2) revealed an unsymmetrical dinuclear complex (FIG. 4). In this case, the coordination geometry of one Ag(I) center was distorted tetrahedral, whereas that of the other Ag(I) center was approximately triangular planar.

TABLE 3

Selected bond distances (Å) and angles (°) for complex (2)

| Complex (2) | | | |
|---|---|---|---|
| Ag1-P1 | 2.4852(9) | Ag2-P3 | 2.3735(11) |
| Ag1-P2 | 2.4751(9) | Ag2-N4 | 2.204(3) |

TABLE 3-continued

Selected bond distances (Å) and angles (°) for complex (2)

| Complex (2) | | | |
|---|---|---|---|
| Ag1-N1 | 2.260(3) | Ag2-N2 | 2.246(3) |
| Ag1-N3 | 2.361(3) | | |
| P2-Ag1-P1 | 121.03(3) | N4-Ag2-P3 | 130.82(9) |
| N1-Ag1-P2 | 121.43(8) | N4-Ag2-N2 | 108.63(12) |
| N1-Ag1-P1 | 107.29(8) | N2-Ag2-P3 | 120.06(8) |
| N1-Ag1-N3 | 95.28(11) | | |
| N3-Ag1-P2 | 102.40(8) | | |
| N3-Ag1-P1 | 104.14(8) | | |

In complex (2), the average Ag—N bond length of 2.311(3) Å at the tetrahedral site was comparable to the corresponding distance in complex (1), while that of the trigonal planar site, 2.225(3) Å, was considerably shorter. The P1-Ag1-P2 angle (tetrahedral site) of 121.03(3°) and the N1-Ag1-N3 angle of complex (2) (95.28(11)°) were comparable to the corresponding values in complex (1). However, the N4-Ag2-N2 angle was noticeably larger (108.63(12)°), consistent with the planar coordination sphere around $Ag_2$ center. A structurally similar complex as complex (2) derived from unsubstituted pyrazole, namely, $[Ag_2(\mu\text{-pz})_2(PPh_3)_3]$ had been reported earlier. In this case the Ag—N bond length at the tetrahedral and the triangular planar sites were 2.309(2) and 2.206(2) Å, respectively, comparable to the values observed in complex (2). The bond angles for both tetrahedral and the planar sites in $[Ag_2(\mu\text{-pz})_2(PPh_3)_3]$ and complex (2) were rather similar. The Ag . . . Ag distance in complex (2) was 3.707(3) Å almost identical with that in $[Ag_2(\mu\text{-pz})_2(PPh_3)_3]$ (3.706(1) Å).

TABLE 4

Selected bond distances (Å) and angles (°) for (3).

| | Complex (3) |
|---|---|
| Ag1-P1 | 2.5017(12) |
| Ag1-P2 | 2.4868(12) |
| Ag1-N1 | 2.307(4) |
| Ag1-N2a | 2.378(4) |
| P2-Ag1-P1 | 120.75(4) |
| N1-Ag1-P2 | 110.74(11) |
| N1-Ag1-P1 | 114.88(11) |
| N1-Ag1-N2a | 96.10(14) |
| N2a-Ag1-P2 | 105.86(11) |
| N2-Ag1-P1 | 104.75(10) |

The a-labeled atoms are generated by the −x + 1, −y + 2, −z + 1 symmetry operation Complex (3) (FIG. 6) was structurally quite similar to complex (1) (FIG. 4). The two Ag atoms in this structure also formed a twisted metallacycle with a Ag . . . Ag distance of 4.305(4) Å. The average Ag—N bond length in complex (3), 2.343(4) Å was similar to that in complex (1) (2.319(2) Å). The P—Ag—P angle in complex (3), 120.75(4) was consistent with that found in complex (1) (118.82(2)°).

TABLE 5

Selected bond distances (Å) and angles (°) for (4)

| Complex (4) | | | |
|---|---|---|---|
| Ag1-P1 | 2.4694(8) | Ag2-P3 | 2.3789(8) |
| Ag1-P2 | 2.4948(8) | Ag2-N5 | 2.187(3) |
| Ag1-N1 | 2.373(3) | Ag2-N2 | 2.278(3) |
| Ag1-N4 | 2.355(3) | | |
| P1-Ag1-P2 | 124.62(3) | N5-Ag2-P3 | 144.74(8) |
| N4-Ag1-P2 | 105.26(8) | N5-Ag2-N2 | 105.06(11) |

TABLE 5-continued

Selected bond distances (Å) and angles (°) for (4)

| Complex (4) | | | |
|---|---|---|---|
| N4-Ag1-P1 | 115.20(7) | N2-Ag2-P3 | 109.14(8) |
| N4-Ag1-N1 | 97.24(11) | | |
| N1-Ag1-P2 | 108.56(8) | | |
| N1-Ag1-P1 | 102.28(8) | | |

The two Ag atoms in complex (4) (FIG. 7) exhibited the same coordination geometry as in complex (2) (FIG. 5) with an average Ag—N bond length of 2.364(3) Å at the tetrahedral site, slightly longer than the corresponding distance in 2, and 2.233(3) Å at the trigonal planar site. At the tetrahedral site of complex (4), the P1-Ag1-P2 and $N_1$-Ag1-$N_4$ angles were 24.62(3°) and (97.24(11)°), respectively, comparable to the corresponding values in complex (2).

Example 10—NMR Spectra

Figure 3:
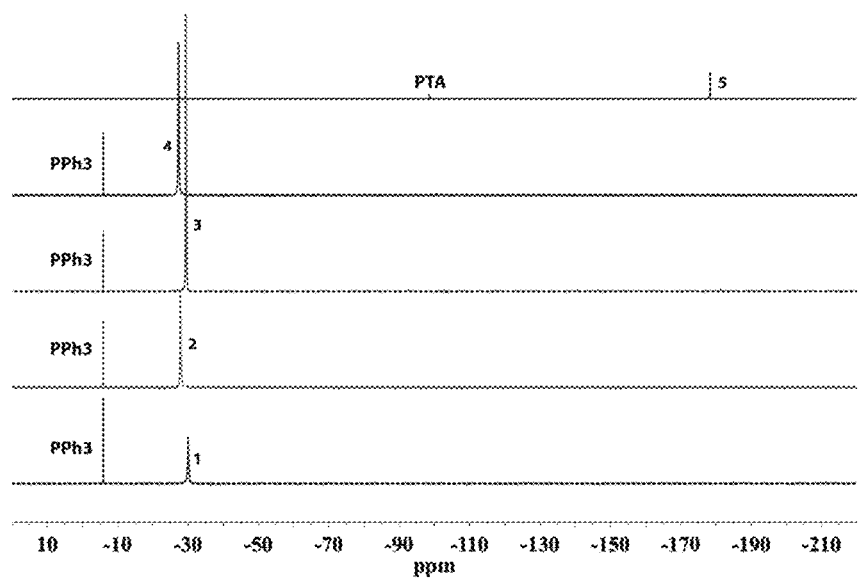
FIG. 3 shows comparative $^{31}P$ NMR spectra for complexes (1-5).

In most cases the solution structure of coordination complexes with substitutionally labile ligands (like $PPh_3$ and PTA in the present case) was different from the solid-state structure. Therefore, $^{31}P\{^1H\}$ NMR studies were performed with complexes (1) to (5) to gain an insight in possible solution characteristics of these complexes. Due to difference in solubility, $^{31}P$ NMR spectroscopy for complexes (1) to (4) was performed in $CDCl_3$ solutions, while the same for complex (5) was carried out in $D_2O$ (due to poor solubility in $CDCl_3$ or $CD_2Cl_2$). For the former complexes $PPh_3$ was used as standard and PTA was employed for the latter one. The substantial kinetic lability of the phosphine ligands often leads to rapid ligand exchange in solution at ambient temperature at the NMR time scale. Indeed, $^{31}P$ NMR spectra of complexes (2) and (4), recorded in the 275-295 K temperature range, consisted of a single resonance resulting from the convergence of the two magnetically non-equivalent $PPh_3$ ligands, revealing the fluxional behavior of these complexes in solution. The comparative $^{31}P$ NMR spectra are shown in FIG. 3. The room temperature $^1H$-NMR spectra of complexes (2) and (4) also showed a single resonance for the pyrazole $H^3$ and $H^5$ protons, in agreement with the $^{31}P$ NMR results.

Example 11—Antibacterial Activity

A skin and soft tissue infection (SSTI) model was used to study the antibacterial properties of three silver complexes. In this model, two layers of agar were employed to mimic a tissue infection with a nutrient rich bottom and the soft-top layer to allow for even dispersal of bacteria. The top soft agar acts like the skin and as bacteria grow they migrate towards the bottom nutrient layer mimicking an infected tissue. Frozen samples of *Pseudomonas Aeruginosa* were thawed and streaked on an agar plate. A single colony was selected and grown in Luria Broth (LB) for 18 h. The suspension was diluted with LB until an A600 (absorbance) of 0.5 was reached. The soft agar bacterial suspension was prepared by adding 120 mL of the above solution to 100 mL 0.8% (w/v) agar with 1% NaCl, which had been autoclaved and cooled to 45° C. before addition. The suspension was gently vortexed and 8 mL was spread evenly on the surface of 20 mL of a 1.5% (w/v) TSB agar plate (100×15 $mm^2$) and allowed to solidify. The plates were incubated for 2 h at 37° C. in order for the bacteria to reach log phase before bactericidal experiments were performed.

Blank KBr pellets (typically utilized for recording IR spectra) and KBr pellets with 2% (w/w) of three complexes (1), (2) and (5), each weighing between 34 and 46 mg, were evenly mulled and pressed with a two-ton load. Three blanks, containing PTA, or 4-Cl-pzH, or $PPh_3$, were also prepared in the same manner. Pellets were carefully placed on the plates (see Example 8) after 2 h of incubation at 37° C. Visible circular zones of bacterial clearing (zone of inhibition) around complex (5) and AgNO3 pellets were observed after incubation at 37° C. for 18 h (FIG. 24). Complex (5) and AgNO3 pellets revealed comparable bacterial clearance even though the KBr pellet with complex (5) contained less silver per weight than the $AgNO_3$ pellet. This superior growth inhibitory performance of complex (5) could in part be due to marginal antibacterial effects of ligands (PTA and 4-Cl-pzH), which showed much smaller but still visible zones of bacterial growth inhibition. The plates containing complexes (1) and (2) exhibited minimal bacterial clearance while $PPh_3$ and KBr (bottom row) showed no zone of inhibition. Also the % (w/w) of Ag and concentration of bio-active silver in plates a), b), e) and f) are listed in Table 6.

The antibacterial efficacy was highly dependent on efficient cellular uptake of the compound. A slightly electronegative surface potential of bacterial cell walls allowed cationic complexes to penetrate relatively easily compared to their neutral analogues All silver(I) complexes were neutral and thereby lacking this advantage, as could be seen from the marginal antibacterial effects of complexes (1) and (2) (FIG. 24). However exceptional growth inhibition of *P. aeruginosa* by complex (5) could be attributed to enhanced cellular uptake of this complex facilitated by the PTA moieties due to their optimal lipophilicity. The bridgehead N atoms of the PTA moiety become protonated under certain physiological conditions and can thereby contribute towards facile cellular uptake and thereafter retention of its complexes. In fact, the adamantane motif can be used in as a "lipophilic bullet" to allow rapid internalization into a variety of cells and tissues. It is interesting to note that the majority of Ag—PTA compounds are polymeric and their bridgehead N atoms also engage in bonding with silver. Therefore, in the subject invention, new discrete dinuclear silver (I) pyrazolido complexes are provided, where PTA is directly coordinated to Ag(I) centers and no further polymeric growth through the N atoms of the PTA moiety occurs.

TABLE 6

Concentration and % (w/w) Ag in each pellet (before diffusion).

| Sample | Conc of Ag in the pellet (M) | % (w/w) Ag in the pellet |
|---|---|---|
| 1 | $1.03548 \times 10^{-6}$ | 0.29394 |
| 2 | $1.26075 \times 10^{-6}$ | 0.35789 |
| 5 | $1.45127 \times 10^{-6}$ | 0.41197 |
| AgNO₃ | $4.47401 \times 10^{-6}$ | 1.27003 |

A previously developed soft tissue infection (SSTI) model has been utilized for the present antibacterial studies. This model mimics the skin in which steady penetration of bacteria to the deeper layer has been achieved using a two-layer agar system that has a soft, evenly dispersed bacterial lawn on the top and a nutrient-rich bottom layer (see Example 11). The gradient causes the bacteria to slowly travel from the slender top layer to the nutrient-rich bottom layer, much alike what would occur in a typical skin infection.

Three complexes (1), (2) and (5) along with 4-Cl-pzH and two the phosphine ligands ($PPh_3$ and PTA) have been assessed for their bactericidal efficacy against a Gram-negative aerobic gamma-proteobacterium namely, *Pseudomonas aeruginosa*. This bacterium is one of the most notorious contributors to the nosocomial infections around the World. During pre-penicillin G era, *Staphylococcus aureus* used to be the most common pathogen responsible in burn wound infections. Although this Gram-positive bacterium still remains one of the sources for such infections, in recent times *P. aeruginosa* has been recognized as major cause of burn wound infections in hospitals. Apart from *P. aeruginosa*, fatal burn wound sepsis can also be instigated through infections caused by *S. aureus* and *A. Baumannii*. However, a very recent study revealed that *P. aeruginosa* infections have the most severe consequences towards burn injuries and often lead to mortality. In the same study, the effect of the burn wound exudates from a group of patients has been investigated on virulence of several pathogens (including *S aureus* and *A. Baumannii*). Interestingly among all the pathogens, *P. aeruginosa* exclusively exhibited normal proliferation within these exudates. In contrast, kinetic studies clearly delineated growth inhibitory effect of the burn wound exudates for other pathogens. Development of therapeutics to combat this nosocomial pathogen deserves urgent attention as with time these microorganisms have developed increasing resistance to antibiotics, particularly in immunocompromised and cystic fibrosis patients.

Silver nitrate and silver sulfadiazine (SSD) are two widely used topical antimicrobial agents for burn wound infections. However, silver nitrate and SSD topical therapeutics suffer from serious limitations: rapid reaction of silver nitrate with biological chloride ions forms insoluble silver chloride and thereby requires continuous administration with the occlusive dressings. Also, although dissociation of silver ions from of SSD is slower compared to that in silver nitrate, poor dermal penetration of this topical agent limits its efficacy on severe burn wound sites. Moreover, a nephrotic syndrome is prevalent within patients receiving topical SSD therapy, due to an allergic reaction associated with the sulfadiazine component.

Therefore, the subject invention provides silver pyrazolido complexes as alternative topical therapeutics against *P. aeruginosa* infections as demonstrated utilizing a SSTI model. The lability of Ag—P bonds, as has been discussed in detail earlier by others, is evident by the NMR spectroscopic behavior of, e.g., complexes (2) and (4). Such lability induces the release of bioactive Ag to the wound sites and, without wanting to be bound by theory, it is believed that the induced release of Ag to the wound is a contributing factor towards the unexpected superior antibacterial activity of complexes of the subject invention, e.g., complex (5).

Therefore, five examples of dinuclear silver(I) pyrazolido complexes (1) to (5) are provided, which complexes are derived from two 4-substituted pyrazole ligands that have been synthesized and structurally characterized according to methods of the subject invention. The highly water-soluble complex (5) incorporating a PTA co-ligand was shown to have unexpected excellent antibacterial activity in a SSTI model against *P. aeruginosa*. The zone of inhibition, which inhibition could be bactericidal or bacteriostatic, in the bacterial culture caused by application of complex (5) is comparable to that for AgNO3. The 4-Cl-pzH ligand shows marginal growth inhibition, in line with the known antimicrobial properties of pyrazoles. The relatively lower efficacy of the two organosoluble complexes (1) and (2) is tentatively attributed to inferior cellular uptake considering all these complexes are neutral in charge.

In contrast, the highly lipophilic nature of the PTA motif, in case, e.g., of complex (5) overwhelms the disadvantage of its dinuclear Ag(I) pyrazolido complex, including the complex being neutral, which is considered unfavorable towards cellular internalization compared to a positively charged analogue.

Furthermore, complex (29) having only a single PTA bound by each silver atom showed surprising superior effectiveness, even compared to the highly anti-bacterial complex (5). Both complex (5) and complex (29) were comparatively tested against P. aeruginosa. The ligands of these complexes displayed no antimicrobial activity and both complexes were readily soluble in water and several bacterial growth media. Complex (5) exhibited a dose-dependent eradication of the bacterial culture with an $IC_{50}$>2000 µg/mL.

In contrast, complex (29) was much more potent and upon application of similar dosages as in case of complex (5) demonstrated already almost 90% eradication of the bacterial culture at the lowest concentration of 31.25 µg/mL tested.

Therefore, while $AgNO_3$ and AgSD are regularly utilized in burn victim wards of hospitals for wound healing purposes, the subject invention provides novel biocompatible silver complexes that have significantly superior effectiveness against bacteria including P. aeruginosa compared to commonly used compounds including, but not limited to, $AgNO_3$ and enable a slow and sustainable delivery of the bio-active silver to the site of interest. Moreover, the biocompatible ligands and co-ligands of the complexes of the subject invention have low toxicity upon the release of $Ag^+$ under physiological environmental conditions.

Advantageously, silver-based dinuclear Ag(I) pyrazolido complexes of the subject invention are a new generation of chemotherapeutics to combat antibiotic resistance and treat bacterial, fungal and viral infections. While the toxicity profile of many nanomaterials towards human health and environment prevents their ready use in vivo, the dinuclear Ag(I) pyrazolido complexes of the subject invention, due to their optimized combination of lipophilic and hydrophilic properties, show unexpected excellent cellular uptake, reduced toxicity and unexpected excellent antibacterial, antifungal and antiviral potency.

We claim:

1. A method of synthesizing a dinuclear silver (I) pyrazolido complex, the method comprising the steps of:
    providing silver oxide ($Ag_2O$) or AgL precursor; wherein AgL is selected from the group consisting of silver acetate, silver benzoate, silver trifluorosulfonate, silver nitrate, and silver chloride;
    providing a pyrazole derivative, wherein the pyrazole derivative comprises independent substituents at $R^3$, $R^4$, and $R^5$ selected from the group consisting of hydrogen, halogen, hydroxyl, nitro, alkyl, alkenyl, aryl, formyl, acetyl, halogen substituted alkyl, halogen substituted aryl, halogen substituted sulfuryl, imine-linked PTA, amine-linked PTA, imine-linked adamantane, amine-linked adamantine, imine-linked triphenylphosphine, and amine-linked triphenylphosphine;
    reacting the pyrazole derivative with the silver oxide or silver precursor in equimolar ratios at ambient conditions to generate a polymer having a general formula of $[Ag(pz^*)]_n$, wherein pz* is a substituted pyrazolido anion; optionally, purifying said polymer; and
    reacting the polymer with a phosphine selected from the group consisting of phosphaadamantane (PA), phenanthrene diphenylphosphine (PDPP), 8-((4-phosphino)phenyl)-4,4-dimethyl-1,3,5,7-tetramethyl-2,6-diethyl-4-bora-3a,4a-diaza-s-indacene (PMBODIPY), 8-((4-phosphino) phenyl)-4,4-diethyl-1,3,5,7-tetramethyl-2,6-diethyl-4-bora-3a,4a-diaza-s-indacene (PEBODIPY), and 8-((4-phosphino) phenyl)-4,4-diphenyl-1,3,5,7-tetramethyl-2,6-diethyl-4-bora-3a,4a-diaza-s-indacene (PPBODIPY).

2. A method of synthesizing a dinuclear silver (I) pyrazolido complex, the method comprising the steps of:
    contacting a 4-R-pyrazolate with silver benzoate in equimolar amounts in dry THF to generate insoluble $[Ag(R-pyrazolate)]_n$ polymers, R being selected from the group consisting of hydrogen, halogen, hydroxyl, nitro, alkyl, alkenyl, aryl, formyl, acetyl, halogen substituted alkyl, halogen substituted aryl, halogen substituted sulfuryl, imine-linked PTA, amine-linked PTA, imine-linked adamantane, amine-linked adamantine, imine-linked triphenylphosphine, and amine-linked triphenylphosphine;
    isolating the insoluble $[Ag(R-pyrazolate)]_n$ polymers;
    reacting the insoluble $[Ag(R-pyrazolate)]_n$ polymers with a phosphine, wherein the phosphine is PA, (4-sulfophenyl)diphenylphosphine (SDPP), PDPP, or PMBODIPY; and optionally;
    washing the dinuclear silver (I) pyrazolido complexes.

3. The method of claim 2, wherein the phosphine is provided in excess or in 1.5 equivalent amounts.

4. The method of claim 2, wherein the phosphine is provided in 2 equivalent amounts.

5. The method of claim 2, wherein the phosphine is provided in 1 equivalent amounts.

6. The method according to claim 1, wherein $R^4$ is selected from the group consisting of hydroxyl, nitro, alkyl, alkenyl, aryl, formyl, acetyl, halogen substituted alkyl, halogen substituted aryl, halogen substituted sulfuryl, imine-linked PTA, amine-linked PTA, imine-linked adamantane, amine-linked adamantine, imine-linked triphenylphosphine, and amine-linked triphenylphosphine.

* * * * *